United States Patent
Cheng et al.

(10) Patent No.: US 10,822,448 B2
(45) Date of Patent: Nov. 3, 2020

(54) DYNAMIC UREA BONDS WITH FAST HYDROLYTIC KINETICS FOR POLYMERS

(71) Applicant: THE BOARD OF TRUSTEES OF THE UNIVERSITY OF ILLINOIS, Urbana, IL (US)

(72) Inventors: Jianjun Cheng, Champaign, IL (US); Kaimin Cai, Champaign, IL (US); Hanze Ying, Champaign, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 76 days.

(21) Appl. No.: 16/082,969

(22) PCT Filed: Mar. 7, 2017

(86) PCT No.: PCT/US2017/021105
§ 371 (c)(1),
(2) Date: Sep. 7, 2018

(87) PCT Pub. No.: WO2017/155958
PCT Pub. Date: Sep. 14, 2017

(65) Prior Publication Data
US 2019/0092898 A1    Mar. 28, 2019

Related U.S. Application Data

(60) Provisional application No. 62/304,964, filed on Mar. 8, 2016.

(51) Int. Cl.
*C08F 290/06* (2006.01)
*A61K 47/34* (2017.01)
(Continued)

(52) U.S. Cl.
CPC .......... *C08G 18/7671* (2013.01); *A61K 47/34* (2013.01); *A61L 17/10* (2013.01);
(Continued)

(58) Field of Classification Search
CPC ............ C08G 18/7671; C08G 18/3228; C08G 18/325; C08G 18/4825; C08G 18/6685;
(Continued)

(56) References Cited

U.S. PATENT DOCUMENTS 3,425,999 A * 2/1969 Axelrood ........... C08G 18/6685
528/76
5,081,212 A * 1/1992 Prass ...................... B05D 1/202
428/411.1
2007/0208157 A1 9/2007 Posey et al.

FOREIGN PATENT DOCUMENTS

WO   2014144539 A1   9/2014

OTHER PUBLICATIONS

Ying et al., JACS, Nov. 18, 2014, Vo. 136, No. 49, pp. 16974-16977.
(Continued)

*Primary Examiner* — William K Cheung
(74) *Attorney, Agent, or Firm* — Dilworth IP, LLC

(57) ABSTRACT

The present invention relates to polymers having dynamic urea bonds and more specifically to polymers having hindered urea bonds (HUBs) with fast hydrolytic kinetics. These urea bonds are aryl-substituted, i.e. aromatic-substituted hindered urea bonds, that demonstrate pH independent hydrolytic kinetics, such that they consistently and rapidly hydrolyze in water from pH 2 to 11. The urea bond dissociation for these materials is generally such that $k_{-1} > h^{-1}$, which is two orders of magnitudes faster than for aliphatic hindered ureas. The present invention also relates to hydrolytically reversible or degradable linear, branched or network polymers incorporating these HUBs and to precursors (Continued)

for incorporation of these HUBs into these polymers. The technology can be applied to and integrated into a variety of polymers, such as polyureas, polyurethanes, polyesters, polyamides, polycarbonates, polyamines, and polysaccharides to make linear, branched, and cross-linked polymers. Polymers incorporating these HUBs can be used in a wide variety of applications including for example, environmentally compatible packaging materials and biomedical applications, such as drug delivery systems and tissue engineering. In other embodiments, the HUBs can be used in self-healing polymers.

27 Claims, 6 Drawing Sheets

(51) Int. Cl.
| | |
|---|---|
| A61L 17/10 | (2006.01) |
| A61L 27/18 | (2006.01) |
| C08J 5/18 | (2006.01) |
| C08G 18/76 | (2006.01) |
| C08G 18/32 | (2006.01) |
| C08G 18/66 | (2006.01) |
| C08G 18/48 | (2006.01) |
| B65D 65/46 | (2006.01) |

(52) U.S. Cl.
CPC ............ *A61L 27/18* (2013.01); *B65D 65/466* (2013.01); *C08F 290/06* (2013.01); *C08G 18/325* (2013.01); *C08G 18/3228* (2013.01); *C08G 18/4825* (2013.01); *C08G 18/6685* (2013.01); *C08J 5/18* (2013.01); *C08G 2220/00* (2013.01); *C08G 2230/00* (2013.01); *C08J 2375/02* (2013.01)

(58) Field of Classification Search
CPC ........ A61K 47/34; A61K 17/10; A61K 27/18; B65D 65/466; C08F 290/06; C08J 5/18; C08J 2375/02
USPC .......................................................... 528/68
See application file for complete search history.

(56) References Cited

OTHER PUBLICATIONS

An et al., Chemical Comm., Jun. 30, 2015, vol. 51, No. 66, pp. 13058-13070.
PCT International Search Report and Written Opinion dated Jun. 20, 2017 from corresponding Application No. PCT/US2017/021105, 11 pages.

* cited by examiner

DYNAMIC UREA BONDS WITH FAST HYDROLYTIC KINETICS FOR POLYMERS

RELATED APPLICATION

This application is a national stage filing under 35 U.S.C. § 371 of international PCT application PCT/US2017/021105, filed Mar. 7, 2017, which claims the benefit under 35 U.S.C. § 119(e) of the filing date of U.S. Provisional Application Ser. No. 62/304,964 filed on Mar. 8, 2016, the disclosure of which is incorporated by reference herein in its entirety.

FEDERAL FUNDING LEGEND

This invention was made with government support under CHE 15-08710 awarded by the National Science Foundation. The government has certain rights in the invention.

FIELD OF THE INVENTION

The present invention relates to polymers having dynamic urea bonds and more specifically to polymers having hindered urea bonds (HUBs) with fast hydrolytic kinetics. These urea bonds are aryl-substituted, i.e. aromatic-substituted hindered urea bonds, that demonstrate pH independent hydrolytic kinetics, such that they consistently and rapidly hydrolyze in water from pH 2 to 11. The urea bond dissociation for these materials is generally such that $k_{-1} > h^{-1}$ is two orders of magnitudes faster than for aliphatic hindered ureas. The present invention also relates to hydrolytically reversible or degradable linear, branched or network polymers incorporating these HUBs and to precursors for incorporation of these HUBs into these polymers. The technology can be applied to and integrated into a variety of polymers, such as polyureas, polyurethanes, polyesters, polyamides, polycarbonates, polyamines, and polysaccharides to make linear, branched, and cross-linked polymers. Polymers incorporating these HUBs can be used in a wide variety of applications including for example, environmentally compatible packaging materials and biomedical applications, such as drug delivery systems and tissue engineering. In other embodiments, the HUBs can be used in self-healing polymers.

BACKGROUND OF THE INVENTION

There is a need in the material and polymer sciences to develop polymeric materials with desired in-use performance characteristics, particularly those that can be hydrolyzed, degraded, or reversibly depolymerized. Such polymers are important to deal with environmental challenges such as waste and landfill concerns. Also, there is the need for materials, particularly in the medical and pharmaceutical field, where such hydrolysis and degradation characteristics would be highly desirable as in drug delivery systems and temporary prostheses.

Differing from polymers formed with strong, irreversible covalent bonds and stable bulk properties, polymers prepared through reversible non-covalent interactions or covalent bonds exhibit various dynamic properties. The dynamic features of reversible polymers have been employed in the design of self-healing, shape-memory, and environmentally adaptive materials. However, non-covalent interactions are relatively weak, with only a few exceptions such as quadruple hydrogen bonding, high valence metal chelation, and host-guest molecular interactions. Dynamic covalent bonds, on the contrary, usually have higher strength and more controllable reversibility.

The amide bond forms the basic structure of numerous biological and commodity polymers, for example nylon and polypeptides, and as such, is one of the most important organic functional groups. It has been hypothesized that the amide bond has relatively high stability due to conjugation effects between the lone electron pair on the nitrogen atom and the pi-electrons on the carbonyl p-orbital. Reversing the amide bond, i.e. amidolysis, usually requires extreme conditions, such as highly basic or acidic conditions and/or high temperatures, or the presence of special reagents, such as catalysts and enzymes.

Introducing bulky substituents has been theorized to create steric hindrance to disturb the orbital co-planarity of the amide bond, which diminishes the conjugation effect and thus weakens the carbonyl-amine interaction. However, the dissociated intermediate from amidolysis, would be a ketene, and if formed would generally be too reactive to provide dynamic reversible formation of the amide bond. To make the carbonyl-amine structure reversible, it is required that the dissociated carbonyl structure be stable under ambient conditions but still highly reactive with amines. One such functional group that satisfies these requirements is the isocyanate group, which can be used to form urea linkages. Isocyanates are generally sufficiently stable under ambient conditions and can react with amines rapidly to form a urea bond, a reaction that has been broadly used in the synthesis of polyureas and poly(urethane-ureas). Therefore, it would be highly desirable to control the reversibility and the kinetics of these urea bonds in polymeric materials.

Many currently available polymeric materials lack both the desired performance characteristics and dynamic properties, as it is difficult to achieve both these properties from conventional polymer technologies. For example, highly covalent cross-linked network polymers generally lack the ability to be recycled, processed and self-healed after cracks have developed. As another example, polyureas constitute an important class of polymers, however, polyureas generally have a very stable bond, are not very soluble, and cannot be recycled and reshaped after polymerization, and may not have the desired hydrolytic and degradation properties.

There is also a need to develop high performance polymers for biomedical applications including drug delivery systems, scaffolds for tissue regeneration, surgical sutures, and transient medical devices and implants, which usually require short functioning times and complete degradation and clearance after use. Also such polymers would be useful for controlled release systems in agroindustry and for degradable, environmentally friendly plastics and packaging materials. Polyesters are the most widely used, conventional hydrolysable materials. A large variety of other hydrolysable polymers bearing orthoester, acetal, ketal, aminal, hemiaminal, imine, phosphoester, and phosphazene bonds have also been reported. However, many of these hydrolysable polymers do not have the desired balance of performance characteristics and degradation kinetics Separate from these challenges there is an overarching question of sustainability and environmental stewardship in the production and use of products. It would be highly desirable to develop polymeric materials having the desired in-use performance characteristics that are biodegradable or that can be readily recycled.

See H. Ying et al, *Dynamic urea bond for the design of reversible and self-healing polymers*, Nature Communications, 5, 3218, published Feb. 5, 2014, and PCT Publication WO 2014/144539 A2, to The Board of Trustees of the University of Illinois, published Sep. 18, 2014, which are both incorporated by reference herein in their entirety.

As seen from the foregoing, it would be highly desirable to have improved polymers. It is apparent there is an ongoing need to develop new polymers that have both desired and controlled dynamic characteristics without compromising other in-use performance properties.

We have surprisingly found that HUBs with an aromatic substituent attached directly to the nitrogen of the urea, with the other nitrogen of the urea having bulky substituents, can be used to prepare polymers, such as water degradable or hydrolysable polymers, having the desired hydrolytic and degradation kinetics. We have also surprisingly found that these aromatic HUBs can be incorporated into a range of precursors to provide an efficient and flexible means for making these polymers, because the desired polymers can be synthesized from the precursor monomers by simple combination and generally without the need for a catalyst.

BRIEF DESCRIPTION OF THE FIGURES

FIG. 1A shows the chemical structure of Ph-tBEU and the hydrolysis product. FIG. 1B shows a plot of ln([urea]/[urea]$_0$)–t in buffer solution at the indicated pH. FIG. 1C shows the pseudo first order hydrolytic constant ($k_{obs}$) of Ph-tBEU. The dotted line marks the measured $k_{-1}$ of the Ph-tBEU under the same condition through exchange with 10 equivalents of t-butyl amine.

FIG. 2A shows the chemical structure of the degradable linear HUB polymer and the hydrolysis degradation product. FIG. 2B shows a representative GPC (gel permeation chromatography) trace of methylene diphenyl diisocyante-N-tertbutyl-N-ethyl urea (MDI-tBEU) polymer before and after water degradation in THF (5% v/v water content) at room temperature, a time zero (0 hours) and 0.5 and 4.5 hours. FIG. 2C shows the relative molecular weight change of MDI-tBEU in 5% buffer-THF solution at room temperature at pH 3, 7, and 11.

FIG. 3A is a schematic illustration of the BT-amine containing gel synthesis and release of BT-amine via HUB bond hydrolysis in aqueous buffer. FIG. 3B shows a release profile of BT-amine from the HUB gel in buffer at pH 5.0, 7.4, and 11.0 at 37° C. analyzed by HPLC. FIG. 3C shows a release profile of fluorescein from the ester gel in buffer at pH 5.0, 7.4, and 11.0 at 37° C. analyzed by HPLC. Data represents averages±standard deviation (n=3).

FIG. 4A depicts the synthesis of a fast hydrolysable MDI-tBEU polymer and a methylene diphenyl diisocyante-N-diethyl urea (MDI-DEU) control polymer. FIG. 4B depicts the relative molecular weight change of the MDI-tBEU polymer and the MDI-DEU control polymer over 4 hours.

SUMMARY OF THE INVENTION

Figure 1A:
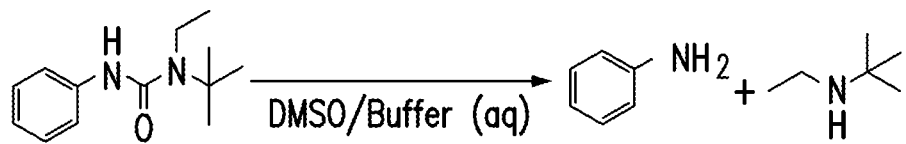
FIGS. 1A to 1C depict the hydrolysis of phenyl-N-tetrabutyl-N-ethyl urea (Ph-tBEU) in 1:1 DMSO-aqueous buffer at various pH conditions at 37° C. as analyzed by HPLC.

The present invention relates to polymers having dynamic urea bonds and more specifically to polymers having hindered urea bonds (HUBs) with fast hydrolytic kinetics. These urea bonds are aryl-substituted, i.e. aromatic-substituted hindered urea bonds, that demonstrate pH independent hydrolytic kinetics, such that they consistently and rapidly hydrolyze in water from pH 2 to 11. The urea bond dissociation for these materials is generally such that $k_{-1} > h^{-1}$, which is two orders of magnitudes faster than for aliphatic hindered ureas. The present invention also relates to hydrolytically reversible or degradable linear, branched or network polymers incorporating these HUBs and to precursors for incorporation of these HUBs into these polymers. The technology can be applied to and integrated into a variety of polymers, such as polyureas, polyurethanes, polyesters, polyamides, polycarbonates, polyamines, and polysaccharides to make linear, branched, and cross-linked polymers. Polymers incorporating these HUBs can be used in a wide variety of applications including for example, environmentally compatible packaging materials and biomedical applications, such as drug delivery systems and tissue engineering. In other embodiments, the HUBs can be used in self-healing polymers.

DETAILED DESCRIPTION OF THE INVENTION

The present invention relates to a hydrolysable polymer comprising a hindered urea bond functional group corresponding to the following Formula (I)

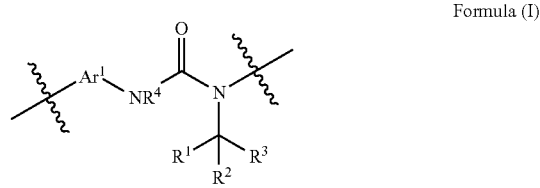

Formula (I)

wherein $R^1$, $R^2$, and $R^3$ are independently selected from —$(C_1-C_{20})$alkyl, —$(C_3-C_{10})$cyclolalkyl, —$(C_1-C_{20})$alkyl $(C_3-C_{10})$cycloalkyl, —$(C_3-C_{10})$cycloalkyl$(C_1-C_{20})$alkyl, —$Ar^2$, —$(C_1-C_{20})$alkyl-$Ar^2$, —$(C_2-C_{20})$alkyl-PEG-$(C_2-C_{20})$ alkyl, and H $R^4$ is selected from H and —$(C_1-C_{20})$alkyl; $Ar^1$ and $Ar^2$ are independently selected from phenyl, naphthyl, a 5 or 6-membered heteroaromatic ring containing one or more heteroatoms selected from nitrogen, oxygen, sulfur, and combinations thereof, and a 7 to 10-membered fused bicyclic heteroaromatic ring containing one or more heteroatoms selected from nitrogen, oxygen, sulfur, and combinations thereof, wherein each $Ar^1$ or $Ar^2$ is optionally substituted with one or more substituents selected from F, Cl, Br, I, —$(C_1-C_8)$alkyl, —$(C_3-C_8)$cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein $R^5$ is selected from H and —$(C_1-C_8)$alkyl.

In another aspect, the present invention relates to a hydrolysable polymer wherein $R^1$, $R^2$, $R^3$, are each methyl.

In another aspect, the present invention relates to a hydrolysable polymer wherein $R^4$ is selected from H, methyl, and ethyl.

In another aspect, the present invention relates to a hydrolysable polymer wherein $R^4$ is selected from H and methyl.

In another aspect, the present invention relates to a hydrolysable polymer wherein $R^4$ is H.

In another aspect, the present invention relates to a hydrolysable polymer wherein $Ar^1$ is selected from phenyl, naphthyl, furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, and imidazopyridyl.

In another aspect, the present invention relates to a hydrolysable polymer wherein $Ar^1$ is phenyl.

In another aspect, the present invention relates to a hydrolysable polymer wherein the hindered urea bond functional group has a $K_{eq}$ that is greater than or equal to $1\times10^4$ $M^{-1}$ at 25° C.

In another aspect, the present invention relates to a hydrolysable polymer wherein the hindered urea bond functional group has a $K_{eq}$ that is greater than or equal to $5\times10^4$ $M^{-1}$ at 25° C.

In another aspect, the present invention relates to a hydrolysable polymer wherein the hindered urea bond functional group has a $K_{eq}$ that is greater than or equal to $1\times10^5$ $M^{-1}$ at 25° C.

In another aspect, the present invention relates to a hydrolysable polymer wherein the hindered urea bond functional group has a $K_{eq}$ that is greater than or equal to $5\times10^5$ $M^{-1}$ at 25° C.

In another aspect, the present invention relates to a hydrolysable polymer wherein the hindered urea bond functional group has a $K_{eq}$ that is less than or equal to $1\times10^8$ $M^{-1}$ at 25° C.

In another aspect, the present invention relates to a hydrolysable polymer wherein the hindered urea bond functional group has a $K_{eq}$ that is less than or equal to $5\times10^7$ $M^{-1}$ at 25° C.

In another aspect, the present invention relates to a hydrolysable polymer wherein the hindered urea bond functional group has a $K_{eq}$ that is less than or equal to $1\times10^7$ $M^{-1}$ at 25° C.

In another aspect, the present invention relates to a hydrolysable polymer wherein the hindered urea bond functional group has a $K_{eq}$ that is less than or equal to $5\times10^6$ $M^{-1}$ at 25° C.

In another aspect, the present invention relates to a hydrolysable polymer wherein the hindered urea bond functional group has a $K_{eq}$ that greater than or equal to $1\times10^4$ $M^{-1}$ and less than or equal to $1\times10^8$ $M^{-1}$ at 25° C.

In another aspect, the present invention relates to a hydrolysable polymer wherein the hindered urea bond functional group has a $k_{-1}$ that is greater than or equal to $1\times10^{-6}$ $h^{-1}$ at 25° C.

In another aspect, the present invention relates to a hydrolysable polymer wherein the hindered urea bond functional group has a $k_{-1}$ that is greater than or equal to $1\times10^{-5}$ $h^{-1}$ at 25° C.

In another aspect, the present invention relates to a hydrolysable polymer wherein the hindered urea bond functional group has a $k_{-1}$ that is greater than or equal to $1\times10^{-4}$ $h^{-1}$ at 25° C.

In another aspect, the present invention relates to a hydrolysable polymer wherein the hindered urea bond functional group has a $k_{-1}$ that is greater than or equal to $1\times10^{-3}$ $h^{-1}$ at 25° C.

In another aspect, the present invention relates to a hydrolysable polymer wherein the hindered urea bond functional group has a $k_{-1}$ that is greater than or equal to $1\times10^{-2}$ $h^{-1}$ at 25° C.

In another aspect, the present invention relates to a hydrolysable polymer wherein the hindered urea bond functional group has a $k_{-1}$ that is greater than or equal to $0.05$ $h^{-1}$ at 25° C.

In another aspect, the present invention relates to a hydrolysable polymer wherein the hindered urea bond functional group has a $k_{-1}$ that is greater than or equal to $0.1$ $h^{-1}$ at 25° C.

In another aspect, the present invention relates to a hydrolysable polymer wherein the hindered urea bond functional group has a $k_{-1}$ that is greater than or equal to $0.5$ $h^{-1}$ at 25° C.

In another aspect, the present invention relates to a hydrolysable polymer wherein the hindered urea bond functional group has a $k_{-1}$ that is greater than or equal to $1$ $h^{-1}$ at 25° C.

In another aspect, the present invention relates to a hydrolysable polymer wherein the hindered urea bond functional group has a $k_1$ that is greater than or equal to $1\times10^4$ $M^{-1}$ $h^{-1}$ at 25° C.

In another aspect, the present invention relates to a hydrolysable polymer wherein the polymer exhibits at least 10% hydrolysis of the hindered urea bond functional groups in the polymer at 24 hours at 25° C.

In another aspect, the present invention relates to a hydrolysable polymer wherein the polymer exhibits at least 20% hydrolysis of the hindered urea bond functional groups at 24 hours at 25° C.

In another aspect, the present invention relates to a hydrolysable polymer wherein the polymer exhibits at least 50% hydrolysis of the hindered urea bond functional groups in the polymer at 24 hours at 25° C.

In another aspect, the present invention relates to a hydrolysable polymer wherein the polymer exhibits a hindered urea bond functional group hydrolysis half-life of less than or equal to 24 hours at 25° C.

In another aspect, the present invention relates to a hydrolysable polymer wherein the polymer exhibits a hindered urea bond functional group hydrolysis half-life of less than or equal to 1.5 hours at 25° C.

In another aspect, the present invention relates to a hydrolysable polymer wherein the polymer exhibits at least 10% hydrolysis of the hindered urea bond functional groups in the polymer at 24 hours at 37° C.

In another aspect, the present invention relates to a hydrolysable polymer wherein the polymer exhibits at least 20% hydrolysis of the hindered urea bond functional groups at 24 hours at 37° C.

In another aspect, the present invention relates to a hydrolysable polymer wherein the polymer exhibits at least 50% hydrolysis of the hindered urea bond functional groups in the polymer at 24 hours at 37° C.

In another aspect, the present invention relates to a hydrolysable polymer wherein the polymer exhibits a hindered urea bond functional group hydrolysis half-life of less than or equal to 24 hours at 37° C.

In another aspect, the present invention relates to a hydrolysable polymer wherein the polymer exhibits a hindered urea bond functional group hydrolysis half-life of less than or equal to 1.5 hours at 37° C.

In another aspect, the present invention relates to a hydrolysable polymer wherein the dissolution occurs at normal room temperature, which is generally about 20 to 25° C.

In another aspect, the present invention relates to a hydrolysable polymer wherein the dissolution occurs at about 37° C.

In another aspect, the present invention relates to a hydrolysable polymer wherein the polymer exhibits a decrease to at least 75 percent of its original molecular weight, such as the number average molecular weight, at normal room temperature after being placed in water for 1 day (24 hours).

In another aspect, the present invention relates to a hydrolysable polymer wherein the polymer exhibits a decrease to at least 50 percent of its original molecular weight, such as the number average molecular weight, at normal room temperature after being placed in water for 1 day (24 hours).

In another aspect, the present invention relates to a hydrolysable polymer wherein the polymer exhibits a decrease to at least 75 percent of its original molecular weight, such as the number average molecular weight, at 37° C. after being placed in water for 1 day (24 hours).

In another aspect, the present invention relates to a hydrolysable polymer wherein the polymer exhibits a decrease to at least 50 percent of its original molecular weight, such as the number average molecular weight, at 37° C. after being placed in water for 1 day (24 hours).

In another aspect, the present invention relates to a hydrolysable polymer that is hydrolysable over the pH range from about 2 to about 11.

In another aspect, the present invention relates to a biodegradable packaging material comprising a hydrolysable polymer.

In another aspect, the present invention relates to a drug delivery system comprising a hydrolysable polymer.

In another aspect, the present invention relates to a medical device comprising a hydrolysable polymer.

In another aspect, the present invention relates to a medical device wherein the medical device is an implantable medical device.

In another aspect, the present invention relates to a surgical suture comprising a hydrolysable polymer.

In another aspect, the present invention relates to a scaffold for tissue regeneration comprising a hydrolysable polymer.

An environmentally degradable packaging, coating, or film comprising a hydrolysable polymer.

In another aspect, the present invention relates to a hydrolysable hindered urea bond-containing polymer comprising recurring units from: (a) a hindered amine monomer containing two or more hindered amine functional groups, and (b) an aromatic isocyanate monomer containing two or more aromatic isocyanate groups.

In another aspect, the present invention relates to a hydrolysable hindered urea bond-containing polymer wherein the hindered amine monomer corresponds to the following Formula (II)

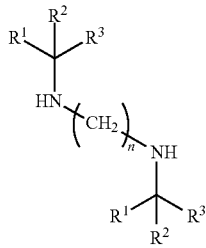

Formula (II)

wherein $R^1$, $R^2$, and $R^3$ are independently selected from —$(C_1-C_{20})$alkyl, —$(C_3-C_{10})$cyclolalkyl, —$(C_1-C_{20})$alkyl$(C_3-C_{10})$cycloalkyl, —$(C_3-C_{10})$cycloalkyl$(C_1-C_{20})$alkyl, —$Ar^2$, —$(C_1-C_{20})$alkyl-$Ar^2$, —$(C_2-C_{20})$alkyl-PEG-$(C_2-C_{20})$alkyl, and H; $Ar^2$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each $Ar^1$ and $Ar^2$ is optionally substituted with one or more substituents selected from F, Cl, Br, I, —$(C_1-C_8)$alkyl, —$(C_3-C_8)$cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein $R^5$ is selected from H and —$(C_1-C_8)$alkyl, and n is an integer from 2 to 100; and wherein the aromatic isocyante monomer corresponds to the following Formula (III)

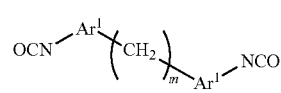

Formula (III)

wherein $Ar^1$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each Ar is optionally substituted with one or more substituents selected from F, Cl, Br, I, —$(C_1-C_8)$alkyl, —$(C_3-C_8)$cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein $R^5$ is selected from H and —$(C_1-C_8)$alkyl. and m is an integer from 0 to 100.

In another aspect, the present invention relates to a hydrolysable hindered urea bond-containing polymer made by a process comprising; (a) reacting a hindered amine monomer containing two or more hindered amine functional groups, and (b) an aromatic isocyante monomer containing two or more aromatic isocyanate groups.

In another aspect, the present invention relates to a hydrolysable hindered urea bond-containing polymer according to claim 24 wherein the hindered amine monomer corresponds to the following Formula (II)

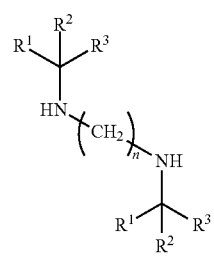

Formula (II)

wherein $R^1$, $R^2$, and $R^3$ are independently selected from —$(C_1-C_{20})$alkyl, —$(C_3-C_{10})$cyclolalkyl, —$(C_1-C_{20})$alkyl$(C_3-C_{10})$cycloalkyl, —$(C_3-C_{10})$cycloalkyl$(C_1-C_{20})$alkyl, —$Ar^2$, —$(C_1-C_{20})$alkyl-$Ar^2$, —$(C_2-C_{20})$alkyl-PEG-$(C_2-C_{20})$alkyl, and H; $Ar^2$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each Ar is optionally substituted with one or more substituents selected from F, Cl, Br, I, —($C_1$-$C_8$)alkyl, —($C_3$-$C_8$)cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein $R^5$ is selected from H and —($C_1$-$C_8$)alkyl, and n is an integer from 2 to 100; and wherein the aromatic isocyante monomer corresponds to the following Formula (III)

Formula (III)

wherein $Ar^1$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each Ar is optionally substituted with one or more substituents selected from F, Cl, Br, I, —($C_1$-$C_8$)alkyl, —($C_3$-$C_8$)cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein $R^5$ is selected from H and —($C_1$-$C_8$)alkyl. and m is an integer from 0 to 100.

In another aspect, the present invention relates to a hydrolysable polymer wherein the hindered urea bond of Formula (I) is in the main polymer chain.

In another aspect, the present invention relates to a hydrolysable polymer wherein the polymer comprises one or more side chains and the hindered urea bond of Formula (I) is in a side chain of the polymer.

In another aspect, the present invention relates to a hydrolysable polymer wherein the polymer is a self-healing polymer Definitions As used herein, the following terms have the indicated meanings unless expressly stated to the contrary.

The term "bulky" as used herein refers to a group or substituent having steric hindrance, especially where the bulky group provides dynamic exchange within a polymer, as described herein. The term "bulky" may be applied to an alkyl, aryl, amino, or other group. Exemplary "bulky alkyl" groups include, but are not limited to isopropyl, tert-butyl, neopentyl, and adamantly. Exemplary "bulky aryl" groups include, but are not limited to, trityl, biphenyl, naphthyl, indenyl, anthracyl, fluorenyl, azulenyl, phenanthrenyl, and pyrenyl. Exemplary "bulky amine" groups include, but are not limited to, tertiary amines substituted with one or more bulky akyl or bulky aryl groups, such as two tert-butyl groups. Exemplary "bulky amide" groups include, but are not limited to, carboxyl groups coupled to a bulky amine.

The term "dynamic bond" or "dynamic bond functional group" refers to a bond or chemical group or functional group that can reversibly form and dissociate. The term "dynamic urea bond" as used herein refers to a urea bond in the polymers herein that can reversibly form and dissociate. Ureas can be represented by the following chemical structure (A):

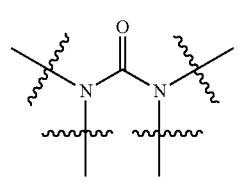

Structure (A)

The hindered urea bonds and the polymers of the present invention are such that the nitrogen or nitrogen atoms of the urea moiety, e.g., as depicted in Structure (A) are such that one of the nitrogen atoms is directly bonded to an aromatic moiety.

In other words, for the urea moiety, one of the nitrogen atoms attached to the carbonyl is directly attached to an aromatic moiety. This aromatic-substituted urea moiety is depicted in Structure (B).

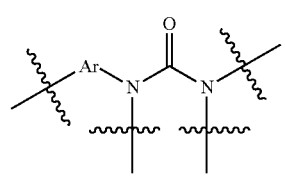

Structure (B)

The terms "$Ar^1$" and "$Ar^2$" are as defined above and in the claims, are intended to be drawn from a wide range of aryl, heteroaryl, aromatic, and heteroaromatic groups. It is recognized that the terms aryl, aromatic, heteroaryl, and heteroaromatic are somewhat interchangeable and also overlap.

The term "highly crosslinked" as used herein refers to a polymer that is extensively cross linked. In such polymers, for example, the average linker length between each crosslinking point can range from 1 to about 100 atoms.

The term "hindered" as used herein refers to a chemical group, such as a hindered bond functional group. In the present invention, a hindered bond functional group includes urea bonds of the present invention that are sterically hindered by one or more bulky groups or substitutents. Furthermore, it is recognized that additional substituents can be described to flank these bonds as further shown in Structures (A) and (B).

The term "hindered urea bond" as used herein refers to a urea bond in a polymer of the present invention that is hindered with one or more bulky groups. It is recognized the "hindered urea bonds" represent a subset of various oxygen, sulfur, and nitrogen-substituted ureas that are considered part of the present invention.

The term "hydrolysable" as used herein means that the hindered bonds or functional groups, such as the hindered urea bonds, can be broken down, or undergo hydrolysis in the presence of water. In its common usage, hydrolysis means the cleavage of chemical bonds by the addition of water. In the presence invention, the hindered bond can undergo hydrolysis.

The term "normal room temperature" means a temperature between about 20 to 25° C.

The term "reversible polymer" as used herein refers to a polymer with blocks or repeating units containing non-covalent or dynamic covalent bonds that can reversibly form and dissociate.

The term "acyl," as used herein alone or as part of another group, denotes the moiety formed by removal of the hydroxy group from the group —COOH of an organic carboxylic acid, e.g., RC(O)—, wherein R is hydrogen, alkyl, aryl, halogen, amino, substituted amino, and the like.

The term "acyloxy," as used herein alone or as part of another group, denotes an acyl group as described above bonded through an oxygen linkage (O), e.g., RC(O)O— wherein R is as defined in connection with the term "acyl."

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., an alkylene). In some embodiments, "alkyl" refers to a fully saturated alkyl. In other embodiments, "alkyl" is branched or unbranched, and is non-cyclic.

The term "alkenyl" as used herein describes groups which are preferably lower alkenyl containing from two to eight carbon atoms in the principal chain and up to 20 carbon atoms. They may be straight or branched chain and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aliphatic" as used herein refers to a chemical compound belonging to the organic class in which the atoms are not linked together to form an aromatic ring. One of the major structural groups of organic molecules, the aliphatic compounds include the alkanes, alkenes, and alkynes, including linear, branched, and cyclic variants, and substances derived from them, actually or in principle, by replacing one or more hydrogen atoms by atoms of other elements or groups of atoms.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The aromatic groups can optionally be substituted. The term "aromatic" encompasses "aryl" groups defined below.

The term "aryl" as used herein refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heteroatom" refers to atoms other than carbon and hydrogen.

The term "heteroaromatic" as used herein optionally substituted aromatic groups having at least one heteroatom in at least one ring, and preferably 5 or 6 atoms in each ring. The term "heteroaromatic" also encompasses "heteroaryl". The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties optionally substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

Generally, the term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —O—, —OR, —SR, —S—, —NR2, —NR3, =NR, —CX3, —CN, —OCN, —SCN, —N=C=O, —NCS, —NO, —NO2, =N2, —N3, —NC(=O)R, —C(=O)R, —C(=O)NRR, —S(=O)2O—, —S(=O)2OH, —S(=O)2R, —OS(=O)2OR, —S(=O)2NR, —S(=O)R, —OP(=O)(OR)2, —P(=O)(OR)2, —OP(=O)(OH)(OR), —P(=O)(OH)(OR), —P(=O)(O—)2, —P(=OXOH)2, —C(=O)R, —C(=O)X, —C(S)R, —C(O)OR, —C(O)O—, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "interrupted" indicates that another group is inserted between two adjacent carbon atoms [and the hydrogen atoms to which they are attached, e.g., methyl (CH3) methylene (CH2) or methine (CH)] of a particular carbon chain being referred to in the expression using the term "interrupted, provided that each of the indicated atom's normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH2O—), carbonyl (—C(=O)—), carboxy (—C(=O)O—), carbonyldioxy (—OC(=O)O—), imine (—C=NH—), sulfinyl (—SO—) and sulfonyl (—SO2-). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached. An alkyl group that is interrupted by a heteroatom therefor forms a heteroalkyl group.

Substituents can include cycloalkylalkyl groups. "Cycloalkylalkyl" may be defined as a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl.

The term "self-healing" as used herein refers to polymers that are able to restore their structure and functionality after damage or fatigue. In other words, breaks or changes in the polymer structure, e.g. bond breaks, can be repaired by bond reformation.

Dynamic Bonds of the Polymers and Precursors

The polymers of the present invention comprise dynamic bonds such as aromatic-substituted hindered urea bonds. Furthermore, the precursors used to make these polymers can in some instances comprise these dynamic bonds or chemical groups that are used to form these dynamic bonds.

For example, the polymers comprise a hindered bond functional group corresponding to the following Formula (I)

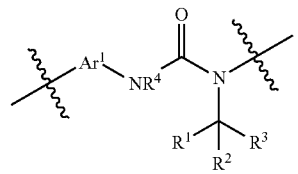

Formula (I)

wherein $R^1$, $R^2$, and $R^3$ are independently selected from —($C_1$-$C_{20}$)alkyl, —($C_3$-$C_{10}$)cycloalkyl, —($C_1$-$C_{20}$)alkyl($C_3$-$C_{10}$)cycloalkyl, —($C_3$-$C_{10}$)cycloalkyl($C_1$-$C_{20}$)alkyl, —$Ar^2$, —($C_1$-$C_{20}$)alkyl-$Ar^2$, —($C_2$-$C_{20}$)alkyl-PEG-($C_2$-$C_{20}$) alkyl, and H;

$R^4$ is selected from H and —($C_1$-$C_{20}$)alkyl;

$Ar^1$ and $Ar^2$ are independently selected from phenyl, naphthyl, a 5 or 6-membered heteroaromatic ring containing one or more heteroatoms selected from nitrogen, oxygen, sulfur, and combinations thereof, and a 7 to 10-membered fused bicyclic heteroaromatic ring containing one or more heteroatoms selected from nitrogen, oxygen, sulfur, and combinations thereof, wherein each $Ar^1$ or $Ar^2$ is optionally substituted with one or more substituents selected from F, Cl, Br, I, —($C_1$-$C_8$)alkyl, —($C_3$-$C_8$)cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein $R^5$ is selected from H and —($C_1$-$C_8$)alkyl.

Polymers

The polymers of the present invention comprise dynamic bonds such as dynamic urea bonds, and more particularly "hindered urea bonds" or "HUBs". The present invention provides polymers having dynamic urea bonds. These polymers include reversible or degradable (e.g., via hydrolysis) linear, branched or network polymers having HUBs. In contrast to traditional hydrolysable polymers, the HUB containing polymers of the present invention could be synthesized from monomers by simple mixing without catalysts. Further background on earlier examples of polymers with dynamic urea bonds are disclosed in PCT Publication WO 2014/144539 A2, to The Board of Trustees of the University of Illinois, published Sep. 18, 2014, which is incorporated by reference herein in its entirety.

Hydrolysable and Reversible Polymers

Hydrolysable polymers are widely used materials that have found numerous applications in the biomedical, agricultural, plastic, and packaging industries. The present invention provides hydrolysable polymers having dynamic bonds such as dynamic urea bonds.

The degradation kinetics could be directly controlled by substituent bulkiness. In contrast to traditional hydrolysable polymers, the HUB containing polymers of the present invention could be synthesized from monomers by simple mixing without catalysts.

Hydrolysable polymers are widely used materials that have found numerous applications in biomedical, agricultural, plastic and packaging industrials. These polymers usually contain ester and other hydrolysable bonds, such as anhydride, acetal, ketal or imine groups in their backbone structures. Here, we describe the design and synthesis of hydrolysable polyureas bearing aromatic-substituted dynamic hindered urea bonds (HUBs) that can reversibly dissociate to bulky amines and isocyanates, the latter of which can be further hydrolyzed by water, driving the equilibrium to facilitate the degradation of polyureas. These aromatic-substituted HUBs are such the kinetics, and resulting properties, are distinguished from those of their aliphatic, i.e. non-aromatic substituted counterparts. Polyureas bearing 1-tert-butyl-1-ethylurea (TBEU) bonds that show high dynamicity (high bond dissociation rates), in the form of either linear polymers or cross-linked gels, can be completely degraded by water under mild conditions. Given the simplicity and low cost for the production of polyureas by simply mixing multifunctional bulky amines and aromatic isocyanates, the versatility of the structures and the tunability of the degradation profiles of HUB-bearing polyureas, these materials have potentially very broad applications.

Over the past few decades, hydrolysable polymeric materials have attracted numerous attentions in both academic and industrial settings. For example, the transient stability of hydrolysable polymers in aqueous solution is critical to their biomedical applications, such as in the design of drug delivery systems, scaffolds for tissue regeneration, surgical sutures, and transient medical devices and implants, which usually require short functioning time and complete degradation and clearance after use. They have also been applied in the design of controlled release systems in agroindustry, and degradable, environmentally friendly plastics and packaging materials. Polyesters are the most widely used, conventional hydrolysable materials. A large variety of other hydrolysable polymers bearing orthoester, acetal, ketal, aminal, hemiaminal, imine, phosphoester, and phosphazene bonds have also been reported. Syntheses of these polymers usually involve condensation polymerization of acyclic monomers or ring-opening polymerization of cyclic monomers, and these syntheses typically involve removal of byproducts, such as water, and use of high reaction temperature or metal catalysts, which can complicate preparation of the material.

Polyureas are commonly used as fiber, coating and adhesive materials. Polyureas can be readily synthesized via addition reaction of widely available, di- or multifunctional isocyanates and amines that do not require the use of catalysts and extreme reaction conditions and do not produce any byproducts. Urea is one of the most stable chemical bonds against further reactions including hydrolysis, due to the conjugation stabilization effects of its dual amide structure. However, urea bonds can be destabilized by incorporating bulky substituents to one of its nitrogen atoms, by means of disturbing the orbital co-planarity of the amide bonds that diminishes the conjugation effect. Urea bonds bearing a bulky substituent, or hindered urea bonds (HUBs), can reversibly dissociate into isocyanate and amines and show interesting dynamic property. The fast reversible reactions between HUBs and isocyanates/amines have been the basis in the design of self-healing polyureas. Because isocyanates can be subject to hydrolysis in aqueous solution to form amines and carbon dioxide, an irreversible process that shifts the equilibrium to favor the HUB dissociation reaction and eventually leads to irreversible and complete degradation of HUBs, can be used to design hydrolysable polymers.

Herein, we report the development of aromatic-substituted HUB-based polyureas that can be hydrolyzed with hydrolytic degradation kinetics tunable by the steric hindrance of the HUB structures.

Polymers with transient stability in aqueous solution, also known as hydrolysable polymers, have been applied in many biomedical applications, such as in the design of drug delivery systems, scaffolds for tissue regeneration, surgical sutures, and transient medical devices and implants. These applications usually require short functioning time, and complete degradation and clearance of materials after their use. Hydrolysable polymers have also been applied in the design of controlled release systems in the agriculture and food industries and used as degradable, environmentally friendly plastics and packaging materials. Besides polyesters, a class of widely used, conventional hydrolysable materials, a large variety of other hydrolysable polymers bearing anhydride, orthoester, acetal, ketal, aminal, hemiaminal, imine, phosphoester, and phosphazene groups have also been reported. Syntheses of these polymers usually involves condensation or ring-opening polymerization, and these syntheses typically involve removal of byproducts and employ high reaction temperature and/or metal catalysts, which complicates the material preparation. We report the design of polyureas bearing hindered urea bonds (HUBs) as potentially one of the least expensive degradable polymers that can be easily synthesized by mixing multifunctional bulky amines and aromatic isocyanates, expanding the family of hydrolysable polymers.

Low cost, high performance hydrolysable polymers are of great potential in biomedical and packaging industries. Certain applications require a constructing material with a degradation profile insensitive to external environment, especially pH, to achieve consistent cargo release under varying conditions. Water degradable materials developed so far generally have pH dependent hydrolytic kinetics on a logarithmic scale that is unable to accomplish the above requirement. We describe a new type of dynamic aryl ureas that hydrolyze consistently fast in water from pH 2 to 11. The pH independent hydrolytic kinetics was shown to be related to the unprecedentedly fast urea bond dissociation ($k_{-1}>1$ $h^{-1}$), which is two orders of magnitude faster than the reported aliphatic hindered ureas. More importantly, hindered aromatic polyureas that have dynamic and fast degradable feature can be easily prepared by addition polymerization from commercial available monomers and resistant to hydrolysis in powder form for months under ambient conditions. The degradation of the polymer was shown to be remarkably fast even at neutral pH.

Water degradable materials have been widely used in a variety of fields including biomedical applications and environmental science. Engineered materials that release encapsulated cargo consistently independent of the surrounding environment, especially the pH environment, have found tremendous significance in the areas of encapsulation and drug delivery. Orally delivered drugs, for example, often have varied in vivo bioavailability and thus uncontrolled therapeutic efficacy, due to the variation of drug release kinetics in response to the change of the gastrointesitnal pH. The hydrolysis of conventional degradable polymers, including esters, anhydrides, orthoesters, carbonates, acetals, and phosphoesters, are generally logarithmically pH dependent. So far, mainly complex formulations achieve pH independent cargo release due to the lack of simple chemistries that can degrade consistently irrespective of pH change over a wide range. In the present invention, we provide fast and pH-independent hydrolysable materials based on hindered aromatic ureas (HAUs)—which is one of the dynamic covalent chemistries. Degradation profiles of the HAUs were shown to be correlated with urea bond dissociation irrespective of the solution pH. Polymeric HAUs were demonstrated to degrade to half their starting molecular weight within ten minutes at room temperature, while ambient storage of the solid polymer powder showed negligible hydrolysis over two months. The transient feature of the HAUs and their facile preparation will have important and practical implications in materials design and applications such as sacrificial coatings, i.e. coatings that are intended to degrade, and biomaterials.

We have shown here that by incorporating a secondary hindered substituent onto the nitrogen atom, the resulting hindered urea bond (HUB) becomes dynamic and can reversibly dissociate into a secondary amine and an isocyanate. The isocyanate can be hydrolyzed to a primary amine, which leads to the breakdown of the HUB by water. Although isocyanate hydrolysis is highly pH dependent, we found that by incorporating an environmentally insensitive urea dissociation as the rate-limiting step, the hydrolysis of this type of "pro-isocyanate" bond can be pH independent. To further achieve faster hydrolytic kinetics, replaced an aliphatic isocyanate with an aryl isocyanate. Aryl amines, as the degradation product of aromatic hindered ureas, have much lowered nucleophilicity than aliphatic amines and potentially generate much less undesired non-dynamic urea side product having low solubility in common solvents Incorporating a secondary substitution onto the nitrogen atom of aliphatic urea bond, the hindered urea bond (HUB) could be reversibly dissociated into amines and isocyanates, thus subject to hydrolysis. The hydrolysis of aliphatic HUB usually results in more than 90% cross-linked ureas via the reaction of the hydrolyzed amine with dissociated isocyanate since the aminolysis is faster than the hydrolysis of isocyanate. The cross-linking of the generated amine-ureas is highly undesired since the resulted polymer is not fully degradable. By replacing the aliphatic isocyanate with aryl isocyanate, the lowered nucleophilicity of the generated aryl amines can avoid the reaction to form cross-linked di-aryl urea and the increased hydrolytic activity of the dissociated aryl isocyanate potentially accelerates the hydrolysis kinetics of the urea materials. Moreover, since the rate determining step in the hydrolysis process is the urea bond dissociation instead of isocyanate hydrolysis, the hydrolytic kinetics of the urea would be first order to the urea concentration independent of solution pH.

Scheme 1 is an illustration of the fast degradable hindered aromatic ureas (HAU).

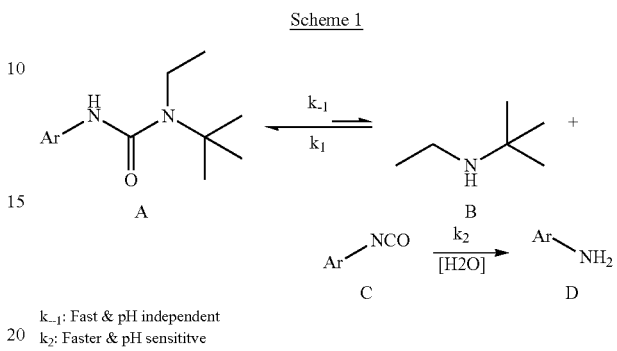

Scheme 1

$k_{-1}$: Fast & pH independent
$k_2$: Faster & pH sensititve

The hydrolytic kinetics is limited by the urea bond dissociation, which is independent of solution pH.

Methods of Preparing Polymers

The disclosure further provides a method for preparing a copolymer comprising dynamic urea moieties. The method comprises contacting an aromatic alkyldiisocyanate and a hindered alkyldiamine in solution, wherein the amines of the alkyldiamine comprise a tert-butyl substituent in a solvent system to form an oligourea. The oligourea is contacted with a trialkanolamine and a polyethylene glycol in the presence of a condensation reaction catalyst, thereby initiating cross-linking. The method provides a cross-linked poly(urea-urethane) polymer having aromatic-substituted hindered urea bonds.

Polymer Characteristics of Keq and Kinetics

To render reversible chemistry dynamic and use the dynamic chemistry for the synthesis of polymers with bulk properties, both the forward and the reverse reaction should be very fast, with large $k_1$ and $k_{-1}$, and the equilibrium favors the formation of the polymer, large $K_{eq}=k_1/k_{-1}$. In the design of dynamic polyurea specifically, it is thus important to identify a hindered urea bond (HUB) with the properly selected substituent on the amine group so that the corresponding HUB can meet the above. For example, equilibrium and exchange studies using 2-isocyanatoethyl methacrylate and amines with different steric hindrance to identify such HUB have been studied. See for example PCT Publication WO 2014/144539 A2, to The Board of Trustees of the University of Illinois, published Sep. 18, 2014, which is incorporated by reference herein in its entirety.

In the present invention, the dynamic hindered aromatic ureas (HAU) are such that they have pH independent degradation profiles and fast neutral hydrolytic kinetics. The urea bond dissociation of HAU is two order of magnitude faster ($k_{-1}>1$ $h^{-1}$) than the reported aliphatic hindered ureas. See, Ying, H.; Zhang, Y.; Cheng, J. Nat. Commun. 2014, 5, 3218, which is incorporated by reference herein in its entirety.

The hindered urea bond functional group has a $K_{eq}$ that is greater than or equal to $1\times10^4$ $M^{-1}$ at 25° C., the hindered urea bond functional group has a $k_{-1}$ that is greater than or equal to 1 $h^{-1}$ at 25° C., and the hindered urea bond functional group has a $k_1$ that is greater than or equal to $1\times10^4$ $M^{-1}$ $h^{-1}$ at 25° C. The resulting hydrolysable polymer exhibits at least 10% hydrolysis of the hindered urea bond functional groups at 24 hours at 37° C. and a hydrolysis half-life of less than or equal to 24 hours, preferably less than or equal to 1.5 hours, at 37° C. The hydrolysable polymer exhibits complete dissolution in an aqueous medium within 10 days, and particularly when the dissolution occurs at normal room temperature.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

The examples show the transferability of the technology for these hindered urea bonds from model molecular systems to their incorporation into polymeric materials.

Example 1: Dynamic Ureas with Fast DH Independent Hydrolytic Kinetics

We designed a set of aryl ureas with distinguished electronic effect on the conjugated phenyl ring (Table 1) and the corresponding $K_{eq}$ were studied by $^1$H NMR through exchanging of the urea with a set of bulky amines in d-chloroform. The equilibrium constant of the aryl urea bond increases as the bulkiness of the substitution on the amine decreases. All of the three t-butyl-ethylureas (tBEU) showed high $K_{eq}$ (>2×10$^4$) and the $K_{eq}$ increases as the phenyl ring becomes more electron deficient (Table 1). The dissociation constant $k_{-1}$ was measured by exchange study of the ureas with another amine and calculated through linear regression. Remarkably, the amine exchange of the tBEU could reach equilibrium within 20 minutes at room temperature in d-chloroform. The $k_{-1}$ of tBEU with aryl substitution is two orders of magnitudes larger than the reported aliphatic urea (Table 1) and among the fastest dynamic chemistries reported so far. In addition, the calculated $k_1$ is larger than $10^5$ M$^{-1}$·h$^{-1}$ indicating that the urea formation can complete within seconds upon mixing. The substituent on the aryl group can remotely affect the HUB through electronic effects, thus offering an extra tunability on the $K_{eq}$ and $k_{-1}$ of the bond, which is unprecedented in hindered urea chemistry. The large value of $K_{eq}$ also makes it possible to prepare large molecular weight aromatic hindered urea materials with quantitative conversion.

We designed a set of aryl ureas with distinguished electronic effect on the conjugated phenyl ring (Table 1) and the corresponding $K_{eq}$ were studied by $^1$H NMR through exchanging of the urea with a set of bulky amines in d-chloroform. The equilibrium constant of the aryl urea bond increases as the bulkiness of the substitution on amine increases. All of the three t-butyl-ethylureas (tBEU) showed comparable $K_{eq}$ (>8×10$^4$) to their aliphatic counterpart with moderate increase as the phenyl ring becomes electron deficient (Table 1). The dissociation constant $k_{-1}$ was measured by exchanging of the ureas with another amine and calculated through linear regression. Remarkably, the amine exchange of the tBEU could be completed within 20 minutes even at room temperature in d-chloroform. The $k_{-1}$ of tBEU with aryl substitution is two orders of magnitudes higher than aliphatic urea (Table 1). In addition, the calculated $k_1$ is larger than $10^5$ M$^{-1}$·h$^{-1}$ indicating the urea formation can be completed within seconds upon mixing. The substituent on the arene can remotely impact the HUB through electronic effect, thus offering tunability on the $K_{eq}$ and $k_{-1}$ of the materials. The large value of $K_{eq}$ make it possible to prepare chemically stable aromatic hindered urea materials with quantitative conversion.

TABLE 1

Equilibrium constant and dissociation rate of different N-t-butyl-N-ethyl ureas (tBEU) in d-chloroform at room temperature.

|  | 1 | 2 | 3 | 4 |
|---|---|---|---|---|
| $K_{eq}$(M$^{-1}$) | 8.1 × 10$^4$ | 3.6 × 10$^5$ | 6.8 × 10$^6$ | 7.9 × 10$^5$ |
| $k_{-1}$(h$^{-1}$) | 11.2 | 8.9 | 5.7 | 0.042 |
| $k_1$(M$^{-1}$·h$^{-1}$) | 9.0 × 10$^5$ | 3.2 × 10$^6$ | 3.9 × 10$^7$ | 3.3 × 10$^4$ |

$k_1$ is calculated as $K_{eq} \times k_{-1}$. The equilibrium constant for the aliphatic HUB (4), below, was adapted from Ying, H., Zhang, Y., Cheng, J., *Nat. Commun.* 2014, 5, 3218, which is incorporated by reference herein in its entirety.

We evaluated the water degradation product of the aryl tBEU in water containing organic solvent. The degradation of the aryl tBEU in de-DMSO were analyzed by $^1$H NMR. All of the three ureas showed fast degradation kinetics with a hydrolysis half-life less than 1.5 hours at 37° C. in 5% water (v/v) containing de-DMSO, which is 10 times fast than an aliphatic HUB under the same condition. In contrast Furthermore, the lowered reactivity of the aryl amines greatly suppresses the formation of stable ureas, as the arylamine and secondary amine were the exclusive degradation products observed when the conjugated aryl structure is electron deficient.

The hydrolysis of aryl tBEU under different pH conditions was then studied in 1:1 DMSO-aqueous buffer solution at 23° C. As being analyzed by HPLC, the 20 degradation of phenyl-tBEU showed remarkably fast degradation throughout all the pH ranges evaluated (FIG. 1C) and the observed hydrolysis constant $k_{obs}$ was independent of pH ranging from 3-11 (FIG. 1C). Fitting of the ln([urea]/[urea]$_0$)–t revealed a linear relationship (R$^2$>0.99) indicating a first-order reaction kinetics (FIG. 1B). More importantly, the apparent hydrolysis constant ($k_{obs}$=0.17 $h^{-1}$) turned out to be equal to the $k_{-1}$ of the urea in the same solvent conditions, which suggested that the hydrolysis of the urea is likely exclusively determined by the dissociation of the HUB instead of the isocyanate hydrolysis. Kinetic analysis of the hydrolytic kinetics confirmed that the overall urea degradation rate is determined by the urea dissociation and can be expressed as $$r(\text{hydrolysis}) = -\frac{d[A]}{dt} = k_{-1}[A]$$

The above equation indicates that the hydrolysis is a first order reaction and the apparent hydrolysis rate $k_{obs}$ is equal to the HAU bond dissociation constant $k_{-1}$, which matched the experimental results.

Figure 2A:
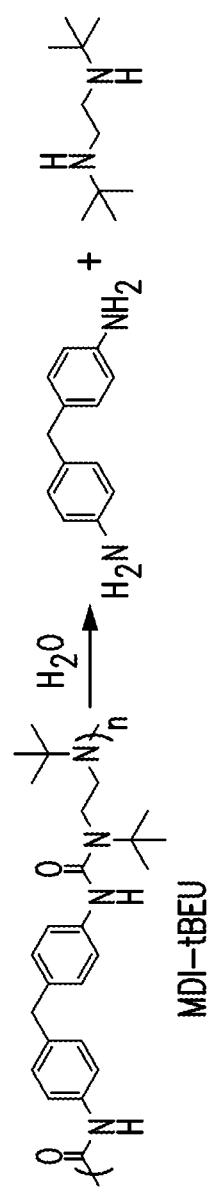
FIGS. 2A to 2C depict the water degradation of an aromatic (i.e. aryl) HUB polymer.
Figure 2C:
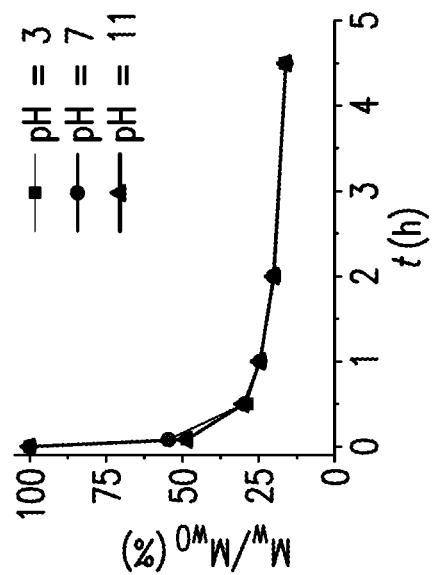

Polymeric HAUs (pHAUs) were then prepared to characterize the hydrolytic feature of HAU in polymeric materials. Considering the wide availability of aryl isocyanates and bulky amines, a large library of pHAU structures can be potentially generated by combination of the two components. As a proof of concept, we adopted a simple alternating polymeric structure by addition polymerization of methylene diphenyl diisocyanate (MDI) and N,N'-di-t-butyl-ethylenediamine at a 1:1 molar ratio (FIG. 2A).

Figure 2B:
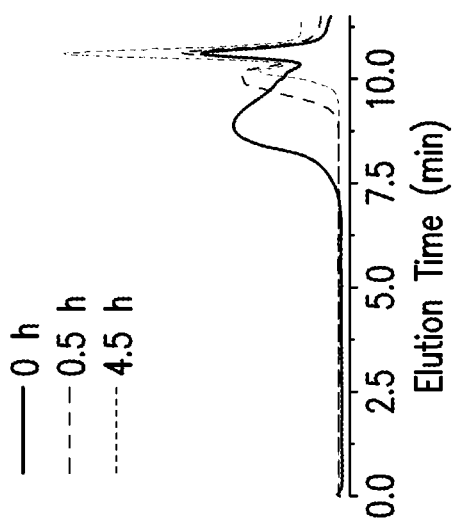

The polymer was then analyzed by gel permeation chromatography (GPC). Based on the calibration with polystyrene standards, the $M_w$ of the MDI-tBEU polymer was calculated to be 4.5 kDa. In the presence of 5% water (v/v) in THF at room temperature (23° C.), the polymer degraded down to less than 50% of the original $M_w$ within 10 minutes (FIG. 2B) while the less bulky N,N-diethyl urea showed a negligible $M_w$ change under the same condition. However, MDI-tBEU polymer was extremely stable under ambient storage conditions. We stored the MDI-tBEU powder in a capped scintillation vial at room temperature. No hydrolytic arylamine product was detected over two months as demonstrated by $^1$H NMR analysis.

In summary, we report a class of dynamic hindered aromatic ureas (HAU) with pH independent degradation profiles and fast neutral hydrolytic kinetics. The urea bond dissociation of HAU is two orders of magnitude faster ($k_{-1}$>1 $h^{-1}$) than the reported corresponding aliphatic hindered ureas and among the fastest dynamic chemistries. The ureas can be easily prepared within minutes by simple mixing of commercially available aryl isocyanates with bulky secondary amines and remain stable in powder form under ambient conditions for months while they can be degraded in the presence of water within tens of minutes in solution, even at neutral pH. The combined features of good stability in the solid state and consistently fast hydrolysis over a range of pH conditions is unprecedented in a simple material. This will have remarkable implications in materials design and applications, such as sacrificial coatings, biomaterials, and surface erosion materials.

Example 2

General Procedures:
Materials

Chemicals were purchased and used as received unless otherwise specified. Anhydrous dimethylformamide (DMF) was dried with a column packed with 4 Å molecular sieves. Tetrahydrofuran (THF) were dried with a column packed with alumina. Phosphate buffered saline (PBS) was purchased from Mediatech, Inc. HPLC grade 0.1% TFA-H$_2$O and acetonitrile were purchased from Fisher Scientific Company LLC (Hanover Park, Ill., USA). All other chemicals were purchased from Sigma-Aldrich (St. Louis, Mo., USA).

Instrumentation

NMR spectra were recorded on a Varian U500 (500 MHz) or VXR-500 (500 MHz) spectrometer. All chemical shifts were reported in part per million (ppm). Tandem gel permeation chromatography (GPC) was performed on a system equipped with an isocratic pump (Model 1200, Agilent Technologies, Santa Clara, Calif., USA), a DAWN HELEOS multi-angle laser light scattering detector (MALLS); (Wyatt Technology, Santa Barbara, Calif., USA), and an Optilab rEX refractive index detector (Wyatt Technology). The detection wavelength of the HELEOS was set at 658 nm. Separations were performed on serially connected size exclusion columns (100 Å, 1000 Å, $10^4$ Å, $10^5$ Å and $10^6$ Å Phenogel columns, 5 μm, 300×7.8 mm, Phenomenex, Torrance, Calif., USA) at 60° C. with DMF containing 0.1 M LiBr as the mobile phase. The HELEOS detector was calibrated with pure toluene without using external polymer standards and was used for the determination of the absolute molecular weights. The molecular weight of polymer was determined from the $d_n/d_c$ value calculated assuming 100% mass recovery, and was processed by ASTRA software (Version 6.1.1, Wyatt Technology). THF GPC was equipped with one column (1000 Å, Phenogel columns, 5 μm, 300× 7.8 mm, Phenomenex, Torrance, Calif., USA) at room temperature and an Optilab rEX refractive index detector (Wyatt Technology). Poly(styrene) standards were used to get a calibration curve of M-elution time. The relative $M_w$ of poly ureas were obtained from the calibration curve. HPLC analysis was conducted by Shimadzu LC system (LC-20AT) connected with PDA detector (SPD-M20A). Phenomenex Kinetex Ph-hexyl column (5 μm, 100 mm×4.6 mm) was used for analysis. A gradient method was adopted using 0.1% TFA-H$_2$O and acetonitrile as mobile phase.

Synthesis of N-t-butyl-N-ethyl-N'-aryl Urea

Aryl isocyanate (0.2 mmol) was mixed with mixed with N-t-butyl-ethylamine (26 mg, 36 μL, 0.26 mmol) in 0.5 mL methylene chloride. The precipitates (hydrolyzed urea/aryl amine from the isocyanate if present) were discarded through centrifugation. Then the solvent was removed completely under vacuum giving white (4-methoxyphenyl and phenyl tBEU)/yellow (4-nitrophenyl tBEU) powder as pure product as confirmed by $^1$H NMR.

Binding Constant Measurement for Aryl Hindered Urea in d-Chloroform.

The binding constant ($K_{eq}$) was measured through indirect method used previously. The $K_{eq}$ of the hindered urea bond increases with the decrease of the substituents bulkiness. Briefly, the of $K_{eq}$ of the equilibrium was measured in d-chloroform and the $K_{eq}$ of each aryl urea was calculated accordingly.

Chemical structure and binding constant measurement of bulky aryl ureas.

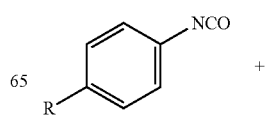

-continued

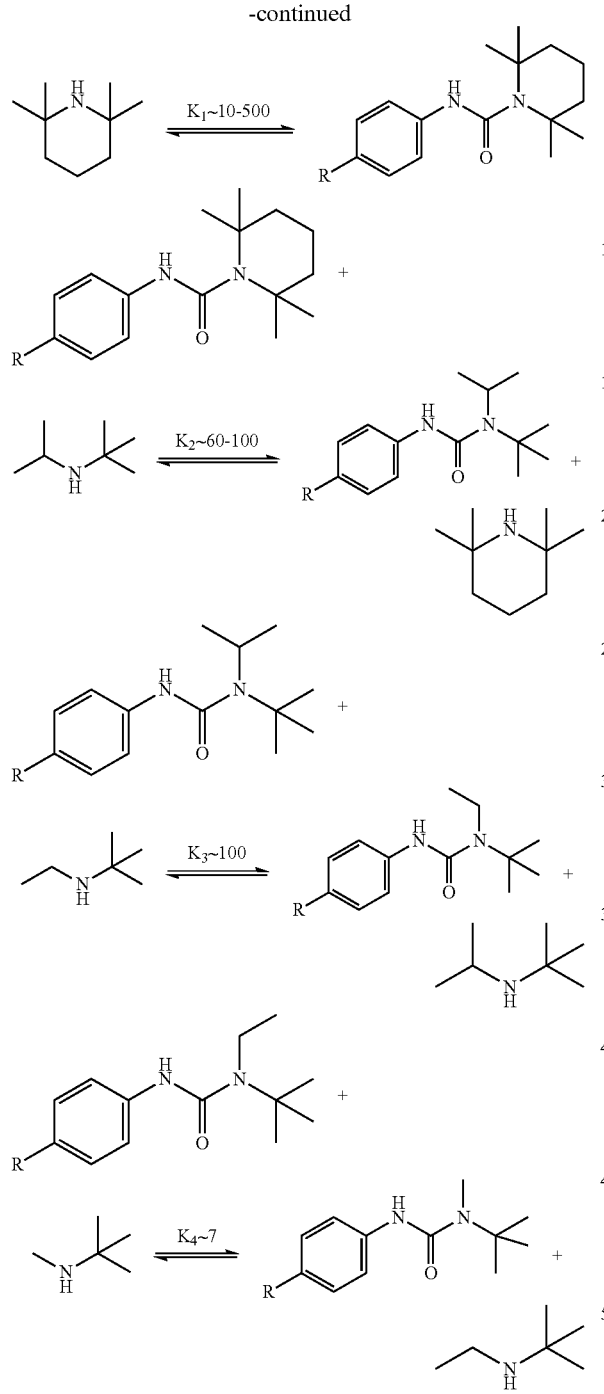

Determination of Dissociation Constant ($k_{-1}$) of Aromatic Hinder Ureas

N-t-butyl-N-ethyl-N'-aryl urea (tBEU)

The dissociation constant ($k_{-1}$) of corresponding hinder ureas were determined through exchange experiment. Briefly, a d-chloroform (550 μL) solution of tBEU (0.050 mmol, ~12 mg) was mixed with N-methyl-t-butyl-amine (1 eq). Then the mixture was monitored with $^1$H NMR. The ratio of the two ureas was quantified by integration of the methyl/methylene hydrogen adjacent to the nitrogen atom. Linear regression of ln $$\left( \frac{[c_{tBEU}]}{[c_{tBEU}]_0} - A \right)$$

~t giving the slope as the dissociation constant ($k_{-1}$).

N,N-diethyl-N'-aryl urea and N-t-ethyl-N-isopropyl-N'-aryl Urea

The method for tBEU was used except that 10 equivalent t-butylamine or n-butyl amine was used.

Determination of hydrolysis kinetics of hindered aromatic urea bonds (HAU) in de-DMSO at 37° C. by $^1$H NMR.

In a typical experiment, 5 mg tBEU was dissolved in 475 μL $d_6$-DMSO and 25 μL $H_2O$. The clear solution was then placed in NMR instrument at 37° C. The composition was constantly monitored by $^1$H NMR every 5 minutes. The urea percent was quantified by ratio of peak integration of the t-butyl group in the urea (9 H, 1.38-1.43 ppm) over t-butyl+ methylene group in the amine (11H, 0.99-1.06 ppm). The cross-linked urea contents were quantified.

HPLC Analysis of pH-tBEU Hydrolysis Kinetics in 50:50 DMSO-$H_2O$ at 37° C.

Ph-tBEU stock solution was prepared in DMSO as 2 mg/mL. The solution was diluted with 1:1 DMSO/buffer to 20 μg/mL (~$10^4$ M) and incubated at 37° C. At specified time, the solution was analyzed by HPLC to quantify the remaining tBEU content by standard calibration curve ($\lambda_{abs}$=264 nm).

The standard sample of Ph-tBEU was prepared by diluting the stock solution with acetonitrile to a 2-fold serial dilution and analyzed instantly after preparation. The pH 1, 7, 10 buffers were prepared by adding acid/base to 1*PBS solution. pH 4 buffer was prepared by citric acid-$Na_2HPO_4$ (0.1 M). The pH of all the buffers were confirmed by pH meter prior to conducting the experiments.

Determination of Ph-tBEU dissociation constant ($k_{-1}$) in 50:50 DMSO-$H_2O$ at 37° C. by HPLC.

To a 1:1 DMSO/$H_2O$ solution of Ph-tBEU (1 mg/mL) was added t-butyl amine (5 μL, ~10 equiv). The clear solution was then incubated in 37° C. incubator. At specified time point, an aliquot of 20 μL was diluted with 980 μL 0.1% TFA-$H_2O$ for HPLC analysis. The Ph-tBEU content was quantified by standard calibration curve. The dissociation constant and half life of the tBEU was calculated through linear regression of $\ln([tBEU]/[tBEU]_0)$-t.

Kinetic Analysis of Dynamic Urea Hydrolysis

The hydrolysis of the urea can be expressed as:

$$r(\text{hydrolysis}) = -\frac{d[A]}{dt} = \frac{d[D]}{dt} = k_2[B][H_2O] \tag{1}$$

Since the isocyanate B is an intermediate with very low concentration during hydrolysis, a steady-state approximation expressed as Equation (2) can thus be deduced:

$$k_2[B][H_2O] + k_1[B][C] = k_{-1}[A] \tag{2}$$

If the protonation of the amine C is considered in aqueous solution, we will have $$[C] = \frac{K_a}{K_a + [H^+]}[C]_t$$

At pH < 10: $\frac{K_a}{K_a + [H^+]} < 0.1$ $$[C] = \frac{K_a}{K_a + [H^+]}[C]_t < 0.1 * 10^{-4} = 10^{-5}$$

$$k_1[B][C] < 10^6 * 10^{-5}[B] = 10^1[B]$$

On the other hand $$k_2[B][H_2O] \approx 10^2 *[B]*10^1 = 10^3[B]$$

Therefore, we have $k_2[B][H_2O] \gg k_1[B][C]$.
The concentration of B can be simplified as $$[B] = \frac{k_{-1}[A]}{k_1[C] + k_2[H_2O]} \approx \frac{k_{-1}[A]}{k_2[H_2O]} \quad (3)$$

The hydrolysis rate of the HAU is $$r(\text{hydrolysis}) = -\frac{d[A]}{dt} = k_2[B][H_2O] = k_{-1}[A] \quad (4)$$

Which is a first order kinetic with the HAU bond dissociation constant as the apparent hydrolysis rate kb, as the urea dissociation is the rate-determining step during hydrolysis.

Synthesis of MDI-tBEU Polymer and Stability Test Under Ambient Condition.

4,4'-Methylene diphenyl diisocyanate (MDI) (100 mg, 0.40 mmol) was mixed with N,N'-di-t-butyl-ethylenediamine (69 mg, 86 µL, 0.40 mmol) in 300 µL chloroform at room temperature for 5 minutes. Then solvent was removed under vacuum pump giving a white powder as polymer. The polymer powder was stored in a 7 ml scintillation vial with cap. The polymer composition was dissolved and analyzed in d-chloroform by $^1$H NMR over 2 month. No peaks were observed in region δ 6.5-6.9 ppm indicating no hydrolytic aryl amine product in the polymer.

Determination of pHAU Hydrolysis Kinetics in Water Containing Organic Solvent.

GPC Characterization of MDI-tBEU Degradation in 5% $H_2O$ Containing THF at Room Temperature.

The stored MDI-tBEU polymer powder was dissolved in THF as 5 mg/mL solution and mixed with 5% v/v $H_2O$. The clear solution was then incubated at 37° C. and the $M_w$ was monitored by THF GPC run at room temperature (one Phenomenex Phenogel 5 u column, $10^3$ Å).

Control Polymer (MDI-DEU) Preparation and Degradation in 5% $H_2O$ Containing DMF at 37° C.

MDI (1.05 g) was mixed with N,N'-di-ethyl ethylene diamine (488 mg) in 2 mL chloroform at room temperature. White precipitates formed immediately and were sonicated for 20 minutes. Then the solvent was removed under vacuum and the polymer was obtained as white powder. The polymer was dissolved in DMF as 5 mg/ml solution and mixed with 5% v/v $H_2O$. The clear solution was then incubated at 37° C. and the $M_w$ was monitored by DMF GPC run at 60° C. The MDI-DEU was not well-dissolved in THF, so DMF was used as solvent for the degradation study instead.

Example 3

Self-Healing Polymer Applications:

Recently, there has been growing interest in the design of dynamic covalent chemistry that can be incorporated with conventional polymers for self-healing applications. Strategies such as double bonds activation by the Grubb's catalyst, high-temperature esterification by metal catalyst, for instance, have been developed. A few catalyst-free, low-temperature dynamic covalent chemistries have also been reported for the synthesis of reversible polymers. See, Lu, Y. X., Guan, Z., *J. AM. Chem. Soc.* 2012, 134, 14226-14231; Lu, Y. X., Toumilhac, F., Leibler, L., Guan, Z., *J. Am. Chem. Soc.* 2012, 134, 8424-8427; Montamal, D., Capelot, M. Toumilhac, F. Leibler, L., *Science* 2011, 334, 965-968; Capelot, M. Montamal, D., Toumilhac, F., Leibler, L., *J. Am. chem. Soc.* 2012, 134, 7664-7667; and Reutenauer, P., Buhler, E., Boul, P. J., Candau, S. J., Lehn, J. M., *Chem. Eur. J.* 2009, 15, 1893-1900, which are all incorporated by reference herein in their entirety.

We report the design of dynamic hindered urea bonds (HUBs) and their applications in the design and synthesis of polyureas and poly(urethane-urea)s, which are capable of catalyst-free dynamic property change and autonomous repairing at 37° C. The self-healing of the fabricated gel showed a distinct temperature dependent behavior as the increasing temperature facilitates the exchange of urea bonds within the polymer structure; however, due to the relative slow exchange kinetics of the aliphatic urea.

We reasoned that by replacing the aliphatic isocyanate with aromatic isocynate, both the urea formation kinetics ($k_1$) should be faster while the equilibrium constant ($K_{eq}$) should be maintained at the same magnitude. Considering the dissociation constant ($k_{-1}$) is derived as $k_1/K_{eq}$, the exchange kinetics of aromatic urea should be faster than that of aliphatic urea. Moreover, by tuning the aromatic ring property especially electron deficiency, both $k_1$ and $K_{eq}$ would increase such that the dissociation ($k_{-1}$) won't be affected much.

We first studied the binding constant of different aromatic isocyanate with bulky secondary amine. 4-methoxylphenyl isocyanate, phenyl isocyanate and 4-nitrophenyl isocyanate were chosen for model studies as they have benzene rings conjugated to isocyanate while their electronic property varies from e rich (MeO-Ph) to e deficient ($NO_2$-Ph). The equilibrium constants of the urea were studied by exchanging the urea with bulky amines one with another. The aromatic ureas have comparable equilibrium constant with aliphatic counterpart.

The dynamic behavior of the aromatic urea was then investigated by exchanging the tBEU with methyl-t-butylamine and the relative concentration of all species were monitored by $^1$H NMR. Surprisingly, the exchange reaction completed within one hour at room temperature for all the 3 three urea. In contrast, the aliphatic tBEU requires several days to reach equilibrium at 37° C. Through linear regression of the exchange component, the dissociate rate of the ureas were determined to be 5-12 $h^{-1}$ at room temperature, which is two order of magnitude higher than the aliphatic counterpart. Notably, as the conjugated benzene ring becomes more electron deficient, the dissociation kinetics decreased while the equilibrium constant increases. Further decrease of the steric hindrance of the amine substitution by diisopropyl group resulted in a compromised urea dissociation ($k_{-1}$~0.035 $h^{-1}$) indicating the aromatic hindered urea follows the same hindrance-dissociation law as its aliphatic counterpart. SeeYing, H.; Zhang, Y.; Cheng, *J. Nat. Commun.* 2014, 5, 3218, which is incorporated by reference herein in its entirety.

Figure 1B:
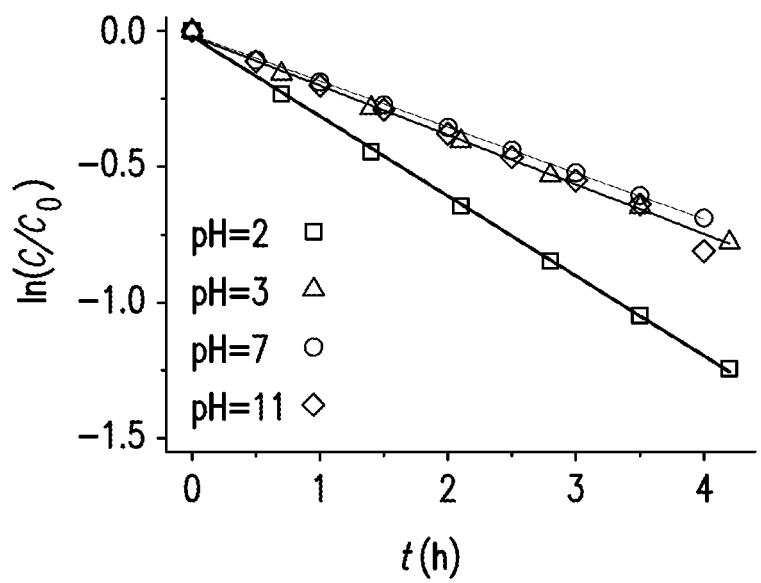
Figure 1C:
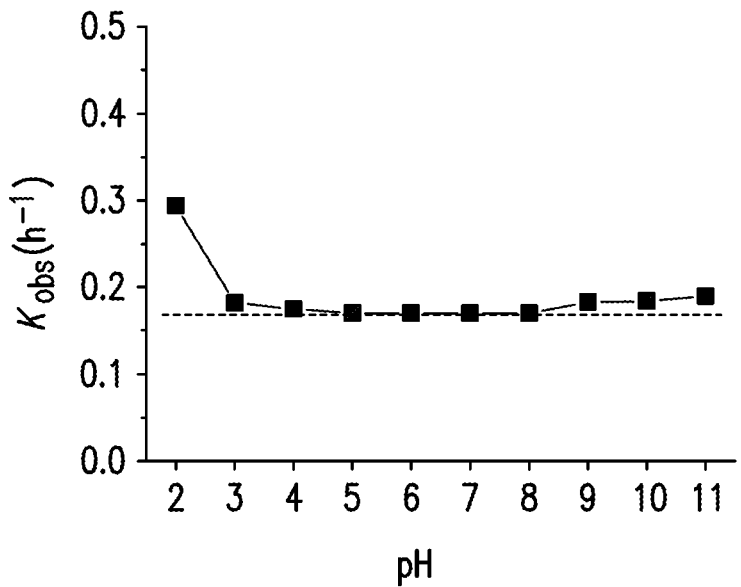

We next studied the dynamic behavior of polyurea prepared by mixing methylene diphenyl diisocyanate (MDI) with N,N'-di-t-butyl-ethylenediamine (TBEDA) at 1:1 ratio in DMF at 30% weight ratio (FIG. 1a). The polyurea was formed with a $M_n$ of $1.3 \times 10^4$ g/mol as analyzed by gel permeation chromatography (GPC) with a mono-modal distribution. After another one equivalent of amine was added into the polymer solution, the polymer gradually degraded at room temperature and reached 50% $M_n$ drop within 1.5 hours as revealed by GPC. In comparison, less hindered polyurea (N,N'-diisopropyl-ethylene diamine+MDI) with much lower exchange constant only showed significant degradation at elevated temperature.

After demonstrating the dynamic property and bond exchange features of HUBs, we next attempted to use HUBs in the design of catalyst-free, low-temperature self-healing materials. Specifically, we designed cross-linked poly(urethanurea)s containing HUBs and tested their self-healing properties. Trihydroxylmethyl propane (THMP) was used as the cross-linker and poly(propylene oxide) ($M_w$=425) was used as the chain extender. Hindered diamines DEA (N,N'-diethyl-ethylenediamine) and TBEDA were used to form the corresponding HUB motifs (DEU and TBEU) in the desired network polymers. THMP, PPO and diamine were allowed to react with MDI in DMF with dibutyltin diacetate (DBTDA) as the catalyst to yield cross-linked poly(urethane-urea). The molar ratio of MDI:diamine:PPO:THMP was set at 10:3:5:1.5 for the synthesis of the self-healing material. The gels behaved as elastomers with good mechanical stiffness (Young's modulus around 1 MPa). The self-healing property of the gels was then tested We cured the polymers in a dog-bone-shaped mould and cut the polymer in the middle by razor blade. After curing at room temperature under ambient condition, the TBEU gel showed fast self-healing due to the fast urea bond exchange. In comparison, the non-dynamic DEU gel showed negligible healing property under the same condition depicting the importance of the dynamic bonding in the healing process.

The hydrolytic stability of the aromatic urea was also demonstrated. Since isocyanate can hydrolyze to corresponding amine, the reversible urea should be able to degrade in the presence of water. We dissolved the urea in 1% water containing de-DMSO and monitored the composition by $^1$H NMR. More than 80% of all the TBEU was degraded into aniline within 2 days while the DIPU turned out to be extremely stable under the same condition even after 40 days.

We studied the reversibility of aromatic hindered ureas with different electron deficiency in detail. The exchange behavior of the aromatic ureas turned out to be much faster than their aliphatic counterparts. Degradability of the aromatic HUB was well demonstrated by both polymer exchange and water hydrolysis. Further, preliminary self-healing test revealed a good self-healing efficiency of the un-optimized organogels.

Example 4

HUB Hydrolysis and Fluorescent Cargo Release

Figure 3A:
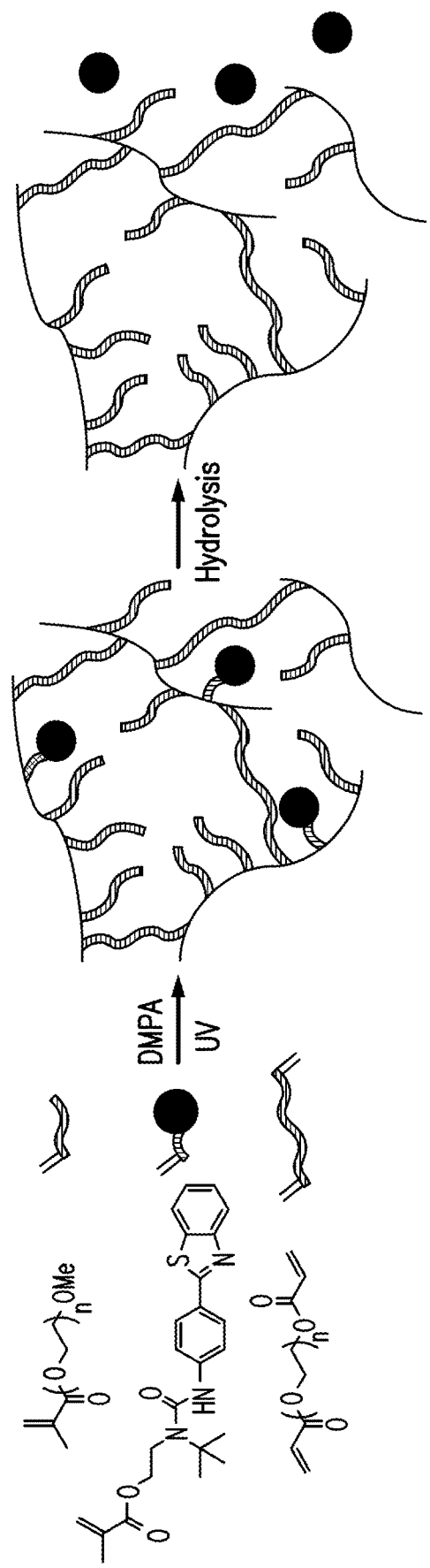
FIGS. 3A to 3C depict the preparation of a degradable organogel by UV cross-linking and release of the fluorescent probe, 2-(4-Aminophenyl)-benzothiazole (BT-amine) and fluorescein via HUB, ester bond hydrolysis, respectively.
Figure 3B:
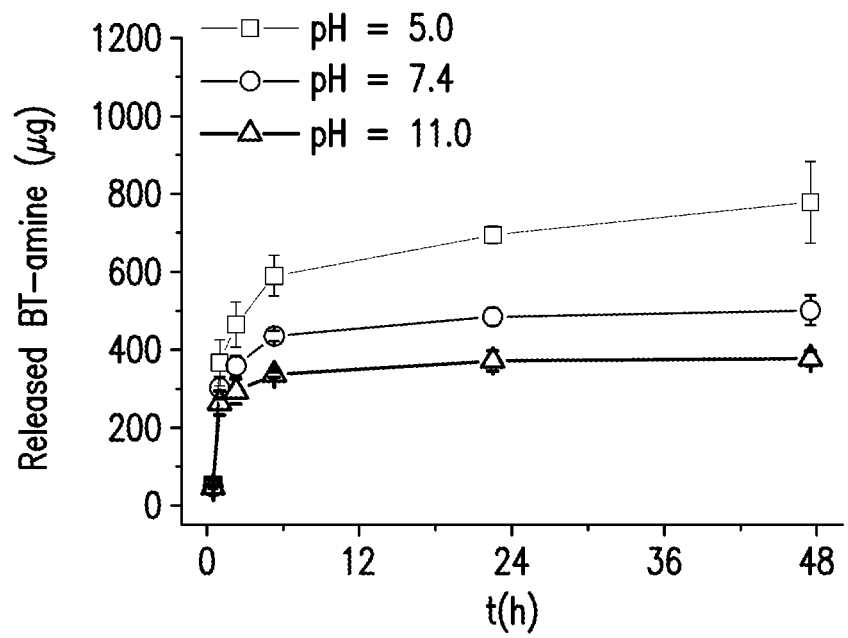
Figure 3C:
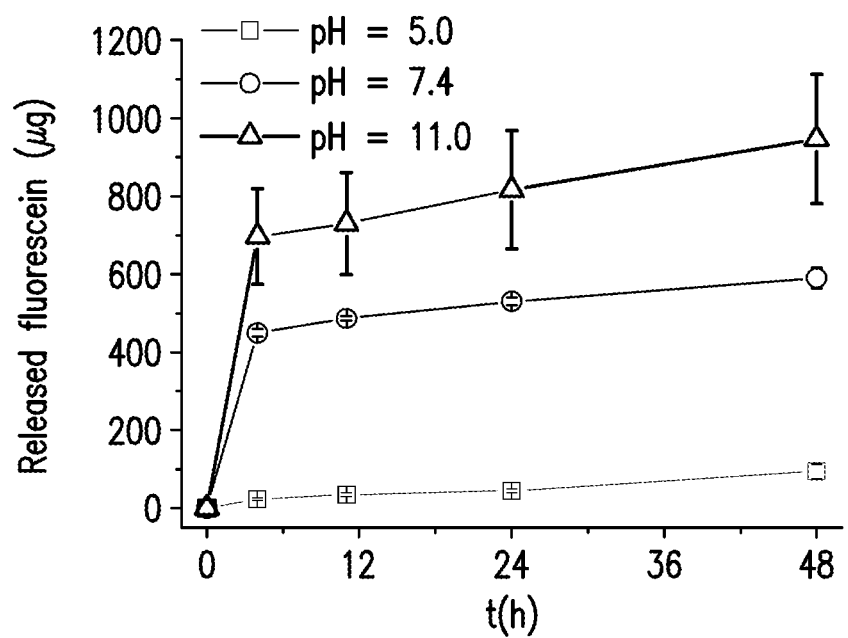
Figure 4A:
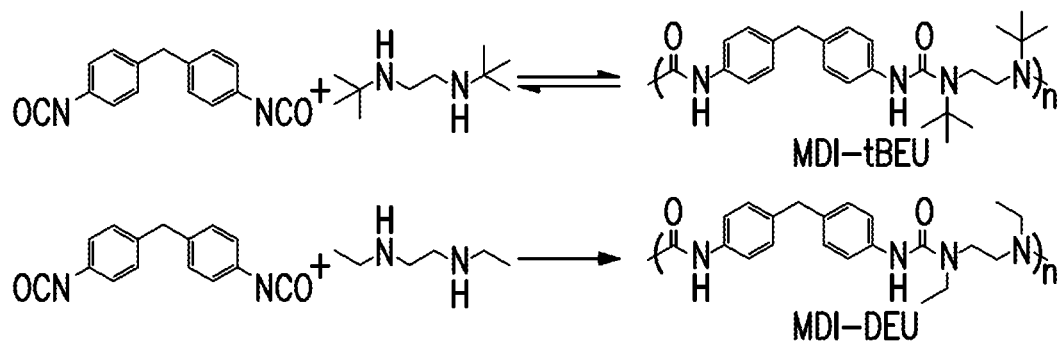
FIGS. 4A and 4B depict the water degradation of an aromatic (i.e. aryl) HUB polymer.
Figure 4B:
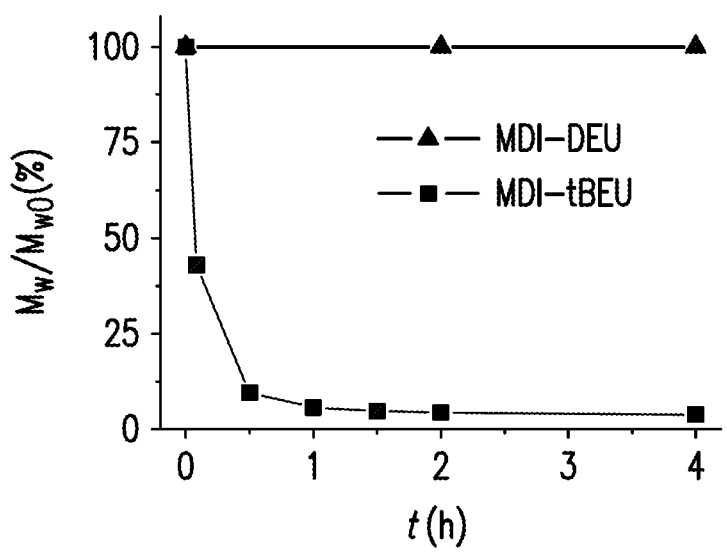

To further explore the potential of the HUB materials for biomedical applications, we tested the HUB hydrolysis and fluorescent cargo release in a gel system. A methacrylate based cross-linked gel was prepared with a fluorescent cargo, 2-(4-Aminophenyl)benzo-thiazole (BT-amine), covalently conjugated to the polyacrylate backbone through HUB bond. The HUB bond can be easily incorporated into methacrylate monomer by reacting t-butyl-aminoethyl methacrylate with isocyanate and the resulting methacrylate can be UV cross-linked with other methacrylate and diacrylate monomers in the presence of 2,2-Dimethoxy-2-phenylacetophenone (DMPA) as the photoiniator (FIG. 3A). A control gel based on fluorescein methacrylate was also prepared to compare the hydrolytic cargo release of ester bond at different pH. The gels were immersed in aqueous buffers of pH 5.0, 7.4 and 11.0 to test the release of conjugated BT-amine and fluorescein at 37° C. The release kinetics of BT-amine was similar over pH 5 to 11 (FIG. 3B). The release of BT-amine was slightly faster in acid medium likely due to the faster diffusion of the protonated BT-amine in acidic environment. In comparison, the control gel with fluorescein methacrylate showed distinctly different release kinetics of fluorescein at different pH—at acid pH, the release of fluorescein was minimal after 2 days while the release was 10 times faster at pH 11 (FIG. 3C).

Synthesis of BTP-HUB-MA

A chloroform suspension (3 mL) of 2-(4-Aminophenyl)benzothiazole (23 mg, 0.10 mmol) was mixed with 15 wt % phosgene toluene solution and refluxed overnight during which the 2-(4-Aminophenyl)benzothiazole gradually dissolved. The solvent and excessive phosgene was removed by pump. The remaining solid was then suspended in DCM (4 mL) and 2-(tert-butylamino)ethyl methacrylate (22 mg, 24 µL, 0.12 mmol) was added, The yellow suspension turned clear within 1 minutes and was concentrated, subject to chromatography (hex:ethyl acetate, 6:1) giving yellow powder as the product (23 mg, yield: 52%). $^1$H NMR (500 MHz, CDCl$_3$), δ 8.08 (s, 1H), 8.02 (3H), 7.87 (d, 2H, J=8.0 Hz), 7.69 (d, 2H, J=9.0 Hz), 7.46 (dd, 1H, J$_1$=J$_2$=8.0 Hz), 7.34 (dd, 1H, J$_1$=J$_2$=8.0 Hz), 6.21 (s, 1H), 5.70 (s, 1H), 4.33 (t, 2H, J=7.0 Hz), 3.56 (t, 2H, J=7.0 Hz), 2.00 (s, 3H), 1.50 (s, 9H). $^{13}$C NMR (126 MHz, CDCl$_3$) δ 168.46, 168.28, 156.17, 154.35, 143.02, 135.74, 134.97, 128.38, 127.59, 127.32, 126.27, 124.87, 122.92, 121.61, 119.50, 64.77, 56.92, 43.26, 29.27, 18.40. HRMS-ESI, (m/z): [M+H]$^+$ calcd for C$_{24}$H$_{28}$N$_3$O$_3$S$^+$, 438.1846; observed, 438.1844.

The following reaction scheme illustrates the synthesis of BTP-HUB-MA.

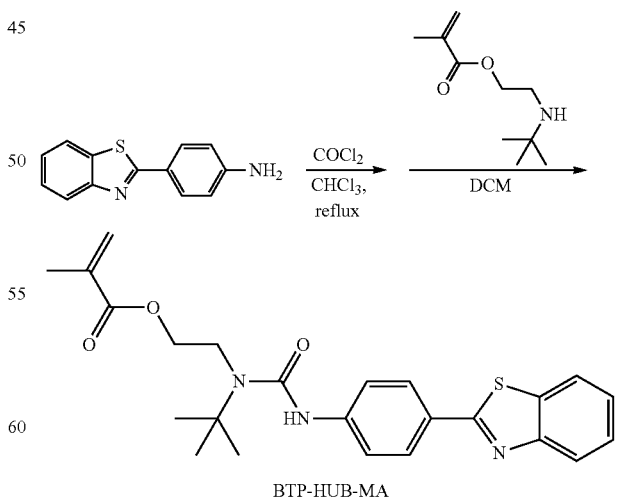

BTP-HUB-MA

The corresponding control gel mentioned above, was made using essentially the procedure as illustrated in FIG. 3A using the following fluorescein methacrylate:

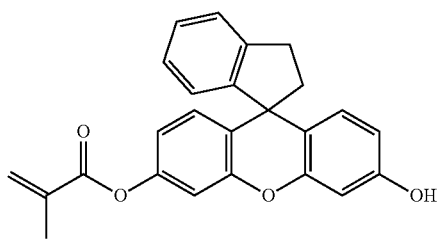

Fluorescein Methacrylate in place of the BTP-HUB-MA:

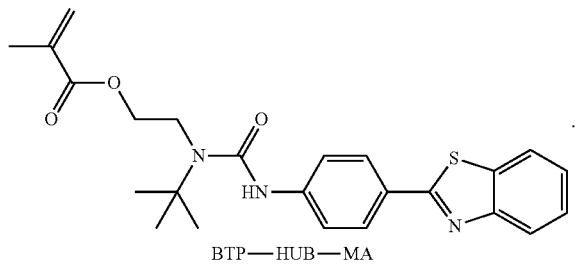

BTP—HUB—MA

Synthesis of BTP-HUB-MA Containing Hydrophilic Cross-Linked Hindered Polyurea Gel Poly(ethylene glycol) methyl ether methacrylate ($M_w$ 475, 950 mg, 2.0 mmol), Poly(ethylene glycol) dimethacrylate ($M_w$ 700, 70 mg, 0.10 mmol), and DMSO solution (20 μL) of BTP-HUB-MA (0.2 mg, 0.0004 mmol) and 2,2-Dimethoxy-2-phenylacetophenone (10 mg, 0.04 mmol) were mixed and irradiated by UV (365 nm, 40 mW/cm$^2$) for 15 min to yield cross-linked gel G1.

BT-Amine Release from Organogel G1

G1 (50 mg) was placed in 15 mL vial and swelled with H$_2$O (10 mL) at 37° C. for 30 minutes. The aqueous suspension was then centrifuged at 6 krpm for 10 minutes. The supernatant was carefully removed and the gel was immersed in 5 mL aqueous buffer cocktail of different pH aforementioned and was stirred vigorously at 37° C. At designated time, an aliquot of 600 μL was removed and centrifuged at 8 krpm for 5 minutes. 500 μL supernatant was taken for HPLC analysis to quantified the 2-(4-Aminophenyl)benzothiazole (BT-amine) ($\lambda_{ex}$=360 nm, $\lambda_{em}$=430 nm) by standard fluorescence calibration curve. The experiment was done in triplicate and the results are presented as mean value±standard deviation.

Synthesis of Fluorescein Methacrylate Containing Hydrophilic Cross-Linked Polyester Gel Poly(ethylene glycol) methyl ether methacrylate ($M_w$ 475, 950 mg, 2.0 mmol), Poly(ethylene glycol) dimethacrylate ($M_w$ 700, 70 mg, 0.10 mmol), and DMSO solution (20 μL) of fluorescein methacrylate (1.0 mg, 0.0025 mmol) and 2,2-Dimethoxy-2-phenylacetophenone (10 mg, 0.04 mmol) were mixed and irradiated by UV (365 nm, 40 mW/cm$^2$) for 15 min to yield cross-linked gel G2.

Fluorescein Release from Organogel G2

G2 (145 mg) was placed in 15 mL vial and swelled with H$_2$O (15 mL) at 37° C. for 30 minutes. The aqueous suspension was then centrifuged at 6 krpm for 10 minutes. The supernatant was carefully removed and the gel was suspended in 15 mL DI H$_2$O. The gel suspension was then separated (1 mL each) into vials, diluted with 4 mL buffer cocktail aforementioned and was stirred vigorously at 37° C. At designated time, an aliquot of 800 μL was removed and centrifuged at 10 krpm for 10 minutes. 600 μL supernatant was taken for HPLC analysis to quantified fluorescein ($\lambda_{ex}$=440 nm, $\lambda_{em}$=532 nm) by standard fluorescence calibration curve. The experiment was done in triplicate and the results are presented as mean value t standard deviation.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight. Also, throughout the disclosure the term "weight" is used. It is recognized the mass of an object is often referred to as its weight in everyday usage and for most common scientific purposes, but that mass technically refers to the amount of matter of an object, whereas weight refers to the force experienced by an object due to gravity. Also, in common usage the "weight" (mass) of an object is what one determines when one "weighs" (masses) an object on a scale or balance.

What is claimed is:

1. A hydrolysable polymer comprising a hindered urea bond functional group corresponding to the following Formula (I)

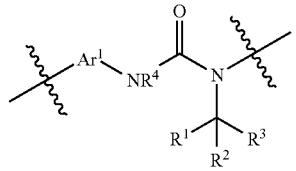

Formula (I)

wherein $R^1$ is selected from —(C$_1$-C$_{20}$)alkyl, —(C$_3$-C$_{10}$)cyclolalkyl, —(C$_1$-C$_{20}$)alkyl(C$_3$-C$_{10}$)cycloalkyl, —(C$_3$-C$_{10}$)cycloalkyl(C$_1$-C$_{20}$)alkyl, —Ar$^2$, —(C$_1$-C$_{20}$)alkyl-Ar$^2$, —C$_2$-C$_{20}$)alkyl-PEG-(C$_2$-C$_{20}$)alkyl, and H;

R$^4$ is selected from H and —(C$_1$-C$_{20}$)alkyl;

Ar$^1$ and Ar$^2$ are independently selected from phenyl, naphthyl, a 5 or 6-membered heteroaromatic ring containing one or more heteroatoms selected from nitrogen, oxygen, sulfur, and combinations thereof, and a 7 to 10-membered fused bicyclic heteroaromatic ring containing one or more heteroatoms selected from nitrogen, oxygen, sulfur, and combinations thereof, wherein each Ar$^1$ or Ar$^2$ is optionally substituted with one or more substituents selected from F, Cl, Br, I, —(C$_1$-C$_8$)alkyl, —(C$_3$-C$_8$)cycloalkyl, —OR$^5$, —CN, —SR$^5$, —SOR$^5$, —SO$_2$R$^5$, —COOR$^5$, —COR$^5$, —CONR$^5$R$^5$, and —NR$^5$COR$^5$—, wherein R$^5$ is selected from H and —(C$_1$-C$_8$)alkyl.

2. A hydrolysable polymer according to claim 1 wherein R$^1$, R$^2$, R$^3$, are each independently selected from —(C$_1$-C$_{20}$)alkyl, —(C$_3$-C$_{10}$)cycloalkyl, —(C$_1$-C$_{20}$)alkyl(C$_3$-C$_{10}$)cycloalkyl, —(C$_3$-C$_{10}$)cycloalkyl(C$_1$-C$_{20}$)alkyl, —Ar$^2$, —(C$_1$-C$_{20}$)alkyl-Ar$^2$, and —C$_2$-C$_{20}$)alkyl-PEG-(C$_2$-C$_{20}$)alkyl.

3. A hydrolysable polymer according to claim 2 wherein R$^1$, R$^2$, R$^3$, are each methyl.

4. A hydrolysable polymer according to claim 3 wherein R$^4$ is selected from H, methyl, and ethyl.

5. A hydrolysable polymer according to claim 3 wherein R$^4$ is H.

6. A hydrolysable polymer according to claim 1 wherein Ar$^1$ is selected from phenyl, naphthyl, furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, and imidazopyridyl.

7. A hydrolysable polymer according to claim 6 wherein Ar$^1$ is phenyl.

8. A hydrolysable polymer according to claim 1 wherein the hindered urea bond functional group has a K$_{eq}$ that is greater than or equal to 1×10$^4$ M$^{-1}$ and less than or equal to 1×10$^8$ M$^{-1}$ at 25° C.

9. A hydrolysable polymer according to claim 1 wherein the hindered urea bond functional group has a k$_{-1}$ that is greater than or equal to 0.05 h$^{-1}$ at 25° C.

10. A hydrolysable polymer according to claim 1 wherein the hindered urea bond functional group has a k$_1$ that is greater than or equal to 1×10$^4$ M$^{-1}$h$^{-1}$ at 25° C.

11. A hydrolysable polymer according to claim 1 wherein the polymer exhibits at least 10% hydrolysis of the hindered urea bond functional groups at 24 hours at 37° C.

12. A hydrolysable polymer according to claim 1 wherein the polymer exhibits a hindered urea bond functional group hydrolysis half-life of less than or equal to 24 hours at 37° C.

13. A hydrolysable polymer according to claim 1 that is hydrolysable over the pH range from about 2 to about 11.

14. A biodegradable packaging material comprising a hydrolysable polymer according to claim 1.

15. A drug delivery system comprising a hydrolysable polymer according to claim 1.

16. A medical device comprising a hydrolysable polymer according to claim 1.

17. A medical device according to claim 16 wherein the medical device is an implantable medical device.

18. A surgical suture comprising a hydrolysable polymer according to claim 1.

19. A scaffold for tissue regeneration comprising a hydrolysable polymer according to claim 1.

20. An environmentally degradable packaging, coating, or film comprising a hydrolysable polymer according to claim 1.

21. A hydrolysable hindered urea bond-containing polymer comprising recurring units from:
(a) a hindered amine monomer containing two or more hindered amine functional groups, and
(b) an aromatic isocyanate monomer containing two or more aromatic isocyanate groups, wherein the hindered amine monomer corresponds to the following Formula (II)

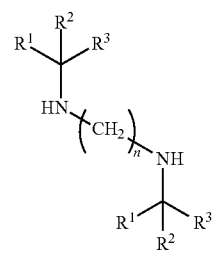

Formula (II)

wherein R$^1$, R$^2$, and R$^3$ are independently selected from —(C$_1$-C$_{20}$)alkyl, —(C$_3$-C$_{10}$)cycloalkyl, —(C$_1$-C$_{20}$)alkyl(C$_3$-C$_{10}$)cycloalkyl, —(C$_3$-C$_{10}$)cycloalkyl(C$_1$-C$_{20}$)alkyl, —Ar$^2$, —(C$_1$-C$_{20}$)alkyl-Ar$^2$, —C$_2$-C$_{20}$)alkyl-PEG-(C$_2$-C$_{20}$)alkyl, and H;

Ar$^2$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each Ar' and Ar$^2$ is optionally substituted with one or more substituents selected from F, Cl, Br, I, —(C$_1$-C$_8$)alkyl, —(C$_3$-C$_8$)cycloalkyl, —OR$^5$, —CN, —SR$^5$, —SOR$^5$, —SO$_2$R$^5$, —COOR$^5$, —COR$^5$, —CONR$^5$R$^5$, and —NR$^5$COR$^5$—, wherein R$^5$ is selected from H and —(C$_1$-C$_8$)alkyl, and n is an integer from 2 to 100; and wherein the aromatic isocyanate monomer corresponds to the following Formula (III)

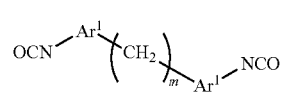

Formula (III)

wherein Ar$^1$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, sulfur, and combinations thereof, wherein each Ar is optionally substituted with one or more substituents selected from F, Cl, Br, I, —(C$_1$-C$_8$)alkyl, —(C$_3$-C$_8$)cycloalkyl, —OR$^5$, —CN, —SR$^5$, —SOR$^5$, —SO$_2$R$^5$, —COOR$^5$, —COR$^5$, —CONR$^5$R$^5$, and —NR$^5$COR$^5$—, wherein $R^5$ is selected from H and —$(C_1-C_8)$alkyl,
and m is an integer from 0 to 100.

22. A hydrolysable hindered urea bond-containing polymer made by a process comprising;
   (a) reacting a hindered amine monomer containing two or more hindered amine functional groups, and
   (b) an aromatic isocyanate monomer containing two or more aromatic isocyanate groups wherein the hindered amine monomer corresponds to the following Formula (II)

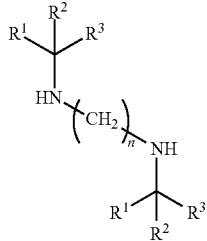

Formula (II)

wherein $R^1$, $R^2$, and $R^3$ are independently selected from —$(C_1-C_{20})$alkyl, —$(C_3-C_{10})$cycloalkyl, —$(C_1-C_{20})$alkyl$(C_3-C_{10})$cycloalkyl, —$(C_3-C_{10})$cycloalkyl$(C_1-C_{20})$alkyl, —$Ar^2$, —$(C_1-C_{20})$alkyl-$Ar^2$, —$(C_2-C_{20})$alkyl-PEG-$(C_2-C_{20})$alkyl, and H;
$Ar^2$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each Ar is optionally substituted with one or more substituents selected from F, Cl, Br, I, —$(C_1-C_8)$alkyl, —$(C_3-C_8)$cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein
$R^5$ is selected from H and —$(C_1-C_8)$alkyl,
and n is an integer from 2 to 100; and
wherein the aromatic isocyanate monomer corresponds to the following Formula (III)

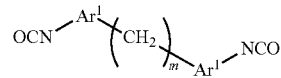

Formula (III)

wherein $Ar^1$ is selected from phenyl, naphthyl, a 5 or 6-membered heteroaromatic ring containing one or more heteroatoms selected from nitrogen, oxygen, sulfur, and combinations thereof, and a 7 to 10-membered heteroaromatic ring or fused bicyclic heteroaromatic ring containing one or more heteroatoms selected from nitrogen, oxygen, sulfur, and combinations thereof, wherein each Ar is optionally substituted with one or more substituents selected from F, Cl, Br, I, —$(C_1-C_8)$alkyl, —$(C_3-C_8)$cycloalkyl, —$OR^5$, —CN, —$SR^5$, —$SOR^5$, —$SO_2R^5$, —$COOR^5$, —$COR^5$, —$CONR^5R^5$, and —$NR^5COR^5$—, wherein
$R^5$ is selected from H and —$(C_1-C_8)$alkyl,
and m is an integer from 0 to 100.

23. A hydrolysable polymer according to claim 1 wherein the hindered urea bond of Formula (I) is in the main polymer chain.

24. A hydrolysable polymer according to claim 1 wherein the polymer comprises one or more side chains and the hindered urea bond of Formula (I) is in a side chain of the polymer.

25. A hydrolysable polymer according to claim 1 wherein the polymer is a self-healing polymer.

26. A hydrolysable hindered urea bond-containing polymer according to claim 21 wherein $R^1$, $R^2$, and $R^3$ are independently selected from —$(C_1-C_{20})$alkyl, —$(C_3-C_{10})$cycloalkyl, —$(C_1-C_{20})$alkyl$(C_3-C_{10})$cycloalkyl, —$(C_3-C_{10})$cycloalkyl$(C_1-C_{20})$alkyl, —$Ar^2$, —$(C_1-C_{20})$alkyl-$Ar^2$, and —$C_2-C_{20})$alkyl-PEG-$(C_2-C_{20})$alkyl.

27. A hydrolysable hindered urea bond-containing polymer according to claim 22 wherein $R^1$, $R^2$, and $R^3$ are independently selected from —$(C_1-C_{20})$alkyl, —$(C_3-C_{10})$cycloalkyl, —$(C_1-C_{20})$alkyl$(C_3-C_{10})$cycloalkyl, —$(C_3-C_{10})$cycloalkyl$(C_1-C_{20})$alkyl, —$Ar^2$, —$(C_1-C_{20})$alkyl-$Ar^2$, and —$C_2-C_{20})$alkyl-PEG-$(C_2-C_{20})$alkyl.

* * * * *